United States Patent
Lang et al.

(10) Patent No.: US 9,072,853 B2
(45) Date of Patent: *Jul. 7, 2015

(54) FOREHEAD PAD FOR RESPIRATORY MASK

(75) Inventors: Bernd Christoph Lang, Graefelfing (DE); Timothy Tsun-Fai Fu, Carlingford (AU); Perry David Lithgow, Moruya (AU); Memduh Guney, Killara (AU); Joanne Elizabeth Drew, Balgowlah Heights (AU); Martin Bechtel, Winsen/Luhe (DE); Achim Biener, Aufkirchen (DE); Michael K. Gunaratnam, Marsfield (AU); Aaron Samuel Davidson, Mona Vale (AU); Milind Chandrakant Raje, Wentworthville (AU)

(73) Assignee: ResMed Limited, Bella Vista (AU)

( * ) Notice: Subject to any disclaimer, the term of this patent is extended or adjusted under 35 U.S.C. 154(b) by 1044 days.

This patent is subject to a terminal disclaimer.

(21) Appl. No.: 12/946,244

(22) Filed: Nov. 15, 2010

(65) Prior Publication Data

US 2011/0056498 A1 Mar. 10, 2011

Related U.S. Application Data

(60) Division of application No. 11/705,451, filed on Feb. 13, 2007, now Pat. No. 7,856,980, which is a continuation of application No. 10/655,595, filed on Sep. 5, 2003, now Pat. No. 7,216,647, and a (Continued)

(51) Int. Cl.
*A62B 18/02* (2006.01)
*A61B 18/08* (2006.01)

(Continued)

(52) U.S. Cl.
CPC ............ *A61M 16/06* (2013.01); *A61M 16/0683* (2013.01); *A61M 16/08* (2013.01);

(Continued)

(58) Field of Classification Search
CPC ............ A61M 16/06; A61M 16/0825; A61M 16/0638; A61M 16/0633; A61M 16/0683; A61M 16/08; A61M 16/0616
USPC ............ 128/201.21, 201.22, 205.25, 206.21, 128/206.24, 206.28, 207.11, 207.13, 128/207.14, 207.18; 24/572.1, 297, 458; 403/252, 291, 360, 375
See application file for complete search history.

(56) References Cited

U.S. PATENT DOCUMENTS

| 4,429 A | 3/1846 | Cooke et al. |
| 35,724 A | 6/1862 | Wilcox |

(Continued)

FOREIGN PATENT DOCUMENTS

| AU | 91/77110 | 11/1991 |
| AU | 94/64816 | 12/1994 |

(Continued)

OTHER PUBLICATIONS

Notification of the Second Office Action mailed Jul. 10, 2012 in Chinese Appln. No. 201010620187.7, with English translation (7 pages).

(Continued)

*Primary Examiner* — Justine Yu
*Assistant Examiner* — Douglas Sul
(74) *Attorney, Agent, or Firm* — Nixon & Vanderhye P.C.

(57) ABSTRACT

A forehead pad for use in a respiratory mask with a forehead support, which includes a base portion to contact a user's forehead, a support post connected to the base portion, and a head adapted to connect the support post to a forehead support. A pair of forehead pads may be joined with a connector.

52 Claims, 27 Drawing Sheets

Related U.S. Application Data continuation-in-part of application No. 10/235,846, filed on Sep. 6, 2002, now Pat. No. 6,823,869.

(60) Provisional application No. 60/424,696, filed on Nov. 8, 2002, provisional application No. 60/467,572, filed on May 5, 2003, provisional application No. 60/317,486, filed on Sep. 7, 2001, provisional application No. 60/342,854, filed on Dec. 28, 2001.

(51) Int. Cl.
  *A61M 16/06* (2006.01)
  *A61M 16/08* (2006.01)

(52) U.S. Cl.
  CPC ....... *A61M16/0825* (2014.02); *A61M 16/0616* (2014.02); *A61M 16/0633* (2014.02); *A61M 16/0638* (2014.02)

(56) References Cited

U.S. PATENT DOCUMENTS

| | | | |
|---|---|---|---|
| 428,592 A | 5/1890 | Chapman | |
| 463,351 A | 11/1891 | Elliott | |
| 592,002 A * | 10/1897 | Denham | 297/405 |
| 715,611 A | 12/1902 | Schnenker et al. | |
| 716,530 A | 12/1902 | Giddens | |
| 781,516 A | 1/1905 | Guthrie | |
| 812,706 A | 2/1906 | Warbasse | |
| 1,070,986 A | 8/1913 | Richter | |
| 1,081,745 A | 12/1913 | Johnston | |
| 1,176,886 A | 3/1916 | Ermold | |
| 1,192,186 A | 7/1916 | Greene | |
| 1,206,045 A | 11/1916 | Smith | |
| 1,333,075 A | 3/1920 | Hill et al. | |
| 1,381,826 A | 6/1921 | Hansen | |
| 1,610,793 A | 12/1926 | Kaufman | |
| 1,632,449 A | 6/1927 | McKesson | |
| 1,653,572 A | 12/1927 | Jackson | |
| 1,672,165 A | 6/1928 | Lewis | |
| 1,733,020 A | 10/1929 | Jones | |
| 1,926,027 A | 9/1933 | Biggs | |
| 2,029,129 A | 1/1936 | Schwartz | |
| 2,033,448 A | 3/1936 | James | |
| 2,123,353 A | 7/1938 | Catt | |
| 2,130,555 A | 9/1938 | Malcom | |
| 2,133,699 A | 10/1938 | Heidbrink | |
| 2,141,222 A | 12/1938 | Pioch | |
| 2,245,658 A | 6/1941 | Erickson | |
| 2,245,969 A | 6/1941 | Francisco et al. | |
| 2,248,477 A | 7/1941 | Lombard | |
| 2,254,854 A | 9/1941 | O'Connell | |
| 2,287,353 A | 6/1942 | Minnick | |
| 2,317,608 A | 4/1943 | Heidbrink | |
| 2,359,506 A | 10/1944 | Battley et al. | |
| 2,371,965 A | 3/1945 | Lehmberg | |
| 2,376,671 A | 3/1945 | Fink | |
| 2,376,871 A | 5/1945 | Fink | |
| 2,382,364 A | 8/1945 | Yant | |
| 2,415,846 A | 2/1947 | Randall | |
| 2,428,451 A | 10/1947 | Emerson | |
| 2,438,058 A | 3/1948 | Kincheloe | |
| 2,454,103 A | 11/1948 | Swidersky | |
| 2,473,518 A | 6/1949 | Garrard et al. | |
| D156,060 S | 11/1949 | Wade | |
| D161,337 S | 12/1950 | Hill | |
| 2,540,567 A | 2/1951 | Bennett | |
| 2,578,621 A | 12/1951 | Yant | |
| 2,590,006 A | 3/1952 | Gordon | |
| 2,617,751 A | 11/1952 | Bickett | |
| 2,625,155 A | 1/1953 | Engelder | |
| 2,638,161 A | 5/1953 | Jones | |
| 2,664,084 A | 12/1953 | Hammermann | |
| 2,693,178 A | 11/1954 | Gilroy | |
| 2,706,983 A | 4/1955 | Matheson et al. | |
| 2,747,464 A | 5/1956 | Bowerman | |
| 2,820,651 A | 1/1958 | Phillips | |
| 2,823,671 A | 2/1958 | Garelick | |
| 2,832,015 A | 4/1958 | Ortega | |
| 2,837,090 A | 6/1958 | Bloom et al. | |
| 2,868,196 A | 1/1959 | Stampe | |
| 2,875,757 A | 3/1959 | Galleher, Jr. | |
| 2,893,387 A | 7/1959 | Gongoll et al. | |
| 2,896,889 A * | 7/1959 | Hershberger et al. | 248/71 |
| 2,902,033 A | 9/1959 | Galleher, Jr. | |
| 2,917,045 A | 12/1959 | Schildknecht et al. | |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,042,035 A | 7/1962 | Coanda | |
| 3,117,574 A | 1/1964 | Replogle | |
| 3,141,213 A | 7/1964 | Nicholas | |
| 3,182,659 A | 5/1965 | Blount et al. | |
| 3,189,027 A | 6/1965 | Bartlett | |
| 3,193,624 A | 7/1965 | Webb et al. | |
| 3,238,943 A | 3/1966 | Holley | |
| 3,288,138 A | 11/1966 | Sachs | |
| 3,315,672 A | 4/1967 | Cunningham et al. | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,456,967 A * | 7/1969 | Hulverson et al. | 24/287 |
| 3,474,783 A | 10/1969 | Ulmann | |
| 3,494,072 A | 2/1970 | Olson | |
| 3,523,534 A | 8/1970 | Nolan | |
| 3,535,810 A | 10/1970 | Baehrle | |
| 3,555,752 A | 1/1971 | Bogaert | |
| 3,556,122 A | 1/1971 | Laerdal | |
| 3,580,051 A | 5/1971 | Blevins | |
| 3,700,000 A | 10/1972 | Hesse et al. | |
| 3,720,235 A | 3/1973 | Schrock | |
| 3,725,953 A | 4/1973 | Johnson et al. | |
| 3,726,275 A | 4/1973 | Jackson et al. | |
| 3,750,333 A | 8/1973 | Vance | |
| 3,752,157 A | 8/1973 | Malmin | |
| 3,796,216 A | 3/1974 | Schwarz | |
| 3,799,164 A | 3/1974 | Rollins | |
| D231,803 S | 6/1974 | Huddy | |
| 3,824,999 A | 7/1974 | King | |
| 3,830,230 A | 8/1974 | Chester | |
| 3,978,854 A | 9/1976 | Mills, Jr. | |
| 4,034,426 A | 7/1977 | Hardwick et al. | |
| 4,049,357 A | 9/1977 | Hamisch, Jr. | |
| 4,062,357 A | 12/1977 | Laerdal | |
| 4,064,875 A | 12/1977 | Cramer et al. | |
| 4,069,516 A | 1/1978 | Watkins, Jr. | |
| 4,077,404 A | 3/1978 | Elam | |
| D248,497 S | 7/1978 | Slosek | |
| 4,111,197 A | 9/1978 | Warncke et al. | |
| D250,131 S | 10/1978 | Lewis et al. | |
| 4,120,302 A | 10/1978 | Ziegler | |
| 4,121,580 A | 10/1978 | Fabish | |
| 4,156,426 A | 5/1979 | Gold | |
| 4,161,946 A | 7/1979 | Zuesse | |
| 4,164,942 A | 8/1979 | Beard et al. | |
| 4,167,185 A | 9/1979 | Lewis | |
| 4,201,205 A | 5/1980 | Bartholomew | |
| 4,226,234 A | 10/1980 | Gunderson | |
| 4,231,363 A | 11/1980 | Grimes | |
| 4,233,972 A | 11/1980 | Hauff et al. | |
| 4,245,632 A | 1/1981 | Houston | |
| 4,248,218 A | 2/1981 | Fischer | |
| 4,265,239 A | 5/1981 | Fischer, Jr. et al. | |
| 4,266,540 A | 5/1981 | Panzik et al. | |
| 4,274,404 A | 6/1981 | Molzan et al. | |
| 4,275,908 A | 6/1981 | Elkins et al. | |
| D262,322 S | 12/1981 | Mizerak | |
| 4,304,229 A | 12/1981 | Curtin | |
| 4,328,797 A | 5/1982 | Rollins et al. | |
| 4,337,767 A | 7/1982 | Yahata | |
| 4,347,205 A | 8/1982 | Stewart | |
| 4,354,488 A | 10/1982 | Bartos | |

(56) References Cited

U.S. PATENT DOCUMENTS

| | | |
|---|---|---|
| 4,369,284 A | 1/1983 | Chen |
| 4,380,102 A | 4/1983 | Hansson |
| 4,402,316 A | 9/1983 | Gadberry |
| 4,412,537 A | 11/1983 | Tiger |
| 4,414,973 A | 11/1983 | Matheson et al. |
| 4,417,575 A | 11/1983 | Hilton et al. |
| 4,446,576 A | 5/1984 | Hisataka |
| 4,454,880 A | 6/1984 | Muto et al. |
| 4,454,881 A | 6/1984 | Huber et al. |
| 4,458,679 A | 7/1984 | Ward |
| 4,467,799 A | 8/1984 | Steinberg |
| 4,494,538 A | 1/1985 | Ansite |
| 4,506,665 A | 3/1985 | Andrews et al. |
| 4,522,639 A | 6/1985 | Ansite et al. |
| 4,549,334 A | 10/1985 | Miller |
| 4,558,710 A | 12/1985 | Eichler |
| 4,572,323 A | 2/1986 | Randall |
| 4,580,556 A | 4/1986 | Kondur |
| 4,593,688 A | 6/1986 | Payton |
| 4,606,340 A | 8/1986 | Ansite |
| D285,496 S | 9/1986 | Berman |
| 4,616,647 A | 10/1986 | McCreadie |
| 4,622,964 A | 11/1986 | Flynn |
| 4,633,972 A | 1/1987 | DeRocher |
| 4,649,908 A | 3/1987 | Ghaly |
| 4,655,213 A | 4/1987 | Rapoport et al. |
| 4,665,570 A | 5/1987 | Davis |
| 4,671,271 A | 6/1987 | Bishop et al. |
| 4,674,134 A | 6/1987 | Lundin |
| 4,676,241 A | 6/1987 | Webb et al. |
| 4,677,975 A | 7/1987 | Edgar et al. |
| 4,677,977 A | 7/1987 | Wilcox |
| 4,686,977 A | 8/1987 | Cosma |
| 4,707,863 A | 11/1987 | McNeal |
| 4,713,844 A | 12/1987 | Westgate |
| D293,613 S | 1/1988 | Wingler |
| 4,732,147 A | 3/1988 | Fuller |
| 4,739,755 A | 4/1988 | White et al. |
| 4,770,169 A | 9/1988 | Schmoegner et al. |
| 4,772,760 A | 9/1988 | Graham |
| 4,774,941 A | 10/1988 | Cook |
| 4,782,832 A | 11/1988 | Trimble et al. |
| 4,783,029 A | 11/1988 | Geppert et al. |
| 4,794,921 A | 1/1989 | Lindkvist |
| 4,799,477 A | 1/1989 | Lewis |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,832,017 A | 5/1989 | Schnoor |
| 4,835,820 A | 6/1989 | Robbins, III |
| 4,841,953 A | 6/1989 | Dodrill |
| 4,848,334 A | 7/1989 | Bellm |
| 4,848,366 A | 7/1989 | Aita et al. |
| 4,850,346 A | 7/1989 | Michel et al. |
| 4,856,118 A | 8/1989 | Sapiejewski |
| D304,384 S | 10/1989 | Derobert |
| 4,870,963 A | 10/1989 | Carter |
| 4,875,714 A | 10/1989 | Lee |
| 4,875,718 A | 10/1989 | Marken |
| 4,898,174 A | 2/1990 | Fangrow, Jr. |
| 4,899,614 A | 2/1990 | Kataumi |
| 4,905,683 A | 3/1990 | Cronjaeger |
| 4,905,686 A | 3/1990 | Adams |
| 4,907,584 A | 3/1990 | McGinnis |
| 4,910,806 A | 3/1990 | Baker et al. |
| 4,915,105 A | 4/1990 | Lee |
| 4,915,106 A | 4/1990 | Aulgur et al. |
| 4,919,128 A | 4/1990 | Kopala et al. |
| 4,938,210 A | 7/1990 | Shene |
| 4,938,212 A | 7/1990 | Snook et al. |
| 4,944,210 A | 7/1990 | Flock et al. |
| 4,944,310 A | 7/1990 | Sullivan |
| 4,946,202 A | 8/1990 | Perricone |
| D310,431 S | 9/1990 | Bellm |
| 4,960,121 A | 10/1990 | Nelson et al. |
| 4,971,051 A | 11/1990 | Toffolon |
| 4,974,586 A | 12/1990 | Wandel et al. |
| 4,986,269 A | 1/1991 | Hakkinen |
| 4,989,271 A | 2/1991 | Sapiejewski et al. |
| 4,989,596 A | 2/1991 | Macris et al. |
| 4,989,599 A | 2/1991 | Carter |
| 4,997,217 A | 3/1991 | Kunze |
| 5,003,631 A | 4/1991 | Richardson |
| 5,003,633 A | 4/1991 | Itoh |
| 5,005,568 A | 4/1991 | Loescher et al. |
| 5,005,571 A | 4/1991 | Dietz |
| 5,018,519 A | 5/1991 | Brown |
| 5,027,809 A | 7/1991 | Robinson |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,054,482 A | 10/1991 | Bales |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| D323,908 S | 2/1992 | Hollister et al. |
| 5,093,940 A | 3/1992 | Nishiyama |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,136,760 A | 8/1992 | Sano et al. |
| 5,137,520 A * | 8/1992 | Maxson et al. ............... 604/180 |
| 5,138,722 A | 8/1992 | Urella et al. |
| 5,140,980 A | 8/1992 | Haughey et al. |
| 5,140,982 A | 8/1992 | Bauman |
| 5,146,914 A | 9/1992 | Sturrock |
| 5,156,146 A | 10/1992 | Corces et al. |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer |
| D334,633 S | 4/1993 | Rudolph |
| 5,199,424 A | 4/1993 | Sullivan et al. |
| D335,322 S | 5/1993 | Jones |
| 5,215,336 A | 6/1993 | Worthing |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,245,995 A | 9/1993 | Sullivan et al. |
| 5,253,641 A | 10/1993 | Choate |
| 5,265,595 A | 11/1993 | Rudolph |
| 5,269,296 A | 12/1993 | Landis |
| 5,279,289 A | 1/1994 | Kirk |
| 5,280,784 A | 1/1994 | Kohler |
| 5,291,880 A | 3/1994 | Almovist et al. |
| 5,301,689 A | 4/1994 | Wennerholm |
| 5,311,862 A | 5/1994 | Blasdell et al. |
| 5,322,057 A | 6/1994 | Raabe et al. |
| 5,322,059 A | 6/1994 | Walther |
| 5,331,691 A | 7/1994 | Runckel |
| 5,334,646 A | 8/1994 | Chen |
| 5,343,878 A | 9/1994 | Scarberry et al. |
| 5,349,949 A | 9/1994 | Schegerin |
| 5,357,945 A | 10/1994 | Messina |
| 5,357,951 A | 10/1994 | Ratner |
| 5,372,130 A | 12/1994 | Stern et al. |
| 5,388,273 A | 2/1995 | Sydor et al. |
| 5,388,571 A | 2/1995 | Roberts et al. |
| 5,390,373 A | 2/1995 | Flory |
| 5,391,248 A | 2/1995 | Brain |
| 5,398,673 A | 3/1995 | Lambert |
| 5,400,781 A | 3/1995 | Davenport |
| 5,404,871 A | 4/1995 | Goodman et al. |
| 5,411,021 A | 5/1995 | Gdulla et al. |
| 5,419,317 A | 5/1995 | Blasdell et al. |
| 5,419,318 A | 5/1995 | Tayebi |
| 5,429,126 A | 7/1995 | Bracken |
| 5,429,683 A | 7/1995 | Le Mitouard |

(56) References Cited

U.S. PATENT DOCUMENTS

| | | |
|---|---|---|
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,485,837 A | 1/1996 | Soles Bee et al. |
| 5,488,948 A | 2/1996 | Dubruille et al. |
| 5,492,116 A | 2/1996 | Scarberry |
| 5,501,214 A | 3/1996 | Sabo |
| 5,509,404 A | 4/1996 | Lloyd et al. |
| 5,511,541 A | 4/1996 | Dearstine |
| 5,517,986 A | 5/1996 | Starr et al. |
| 5,522,382 A | 6/1996 | Sullivan et al. |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,684 A | 11/1996 | Behr |
| 5,570,689 A | 11/1996 | Starr et al. |
| 5,571,217 A | 11/1996 | Del Bon et al. |
| D377,089 S | 12/1996 | Starr et al. |
| 5,592,938 A | 1/1997 | Scarberry et al. |
| 5,608,647 A | 3/1997 | Rubsamen et al. |
| 5,617,849 A | 4/1997 | Springett et al. |
| 5,642,730 A | 7/1997 | Baran |
| 5,645,049 A | 7/1997 | Foley et al. |
| 5,645,054 A | 7/1997 | Cotner et al. |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,174 A | 8/1997 | Jacobelli |
| 5,662,101 A | 9/1997 | Ogden et al. |
| 5,666,946 A | 9/1997 | Langenback |
| 5,676,133 A | 10/1997 | Hickle et al. |
| D385,960 S | 11/1997 | Rudolph |
| 5,685,296 A | 11/1997 | Zdrojkowski et al. |
| 5,687,715 A * | 11/1997 | Landis et al. ............ 128/207.18 |
| 5,704,345 A | 1/1998 | Berthon-Jones et al. |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,740,795 A | 4/1998 | Brydon |
| 5,743,414 A | 4/1998 | Baudino |
| 5,746,201 A | 5/1998 | Kidd |
| 5,794,617 A | 8/1998 | Brunell et al. |
| D398,987 S | 9/1998 | Cotner et al. |
| 5,813,423 A | 9/1998 | Kirchgeorg |
| 5,832,918 A | 11/1998 | Pantino |
| 5,839,436 A | 11/1998 | Fangrow et al. |
| D402,755 S | 12/1998 | Kwok |
| 5,860,677 A | 1/1999 | Martins et al. |
| RE36,165 E | 3/1999 | Behr |
| 5,884,624 A | 3/1999 | Barnett et al. |
| 5,896,857 A | 4/1999 | Hely et al. |
| 5,906,199 A | 5/1999 | Budzinski |
| 5,909,732 A | 6/1999 | Diesel et al. |
| 5,921,239 A | 7/1999 | McCall et al. |
| 5,935,136 A | 8/1999 | Hulse et al. |
| 5,937,851 A | 8/1999 | Serowski et al. |
| 5,966,745 A | 10/1999 | Schwartz et al. |
| 5,975,079 A | 11/1999 | Hellings et al. |
| 5,979,025 A | 11/1999 | Horng |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,029,660 A | 2/2000 | Calluaud et al. |
| 6,029,665 A | 2/2000 | Berthon-Jones |
| 6,029,668 A | 2/2000 | Freed |
| 6,039,044 A | 3/2000 | Sullivan |
| D423,096 S | 4/2000 | Kwok |
| 6,044,844 A | 4/2000 | Kwok et al. |
| 6,062,148 A | 5/2000 | Hodge et al. |
| 6,062,221 A | 5/2000 | Brostrom et al. |
| 6,082,360 A | 7/2000 | Rudolph et al. |
| 6,091,973 A | 7/2000 | Colla et al. |
| D428,987 S | 8/2000 | Kwok |
| 6,098,205 A | 8/2000 | Schwartz et al. |
| 6,112,746 A * | 9/2000 | Kwok et al. ............ 128/207.13 |
| 6,119,693 A * | 9/2000 | Kwok et al. ............ 128/207.11 |
| 6,123,071 A | 9/2000 | Berthon-Jones et al. |
| 6,152,137 A | 11/2000 | Schwartz et al. |
| 6,189,532 B1 | 2/2001 | Hely et al. |
| 6,192,886 B1 | 2/2001 | Rudolph |
| D439,326 S | 3/2001 | Hecker et al. |
| 6,196,223 B1 | 3/2001 | Belfer et al. |
| D443,355 S | 6/2001 | Gunaratnam et al. |
| 6,240,605 B1 | 6/2001 | Stevens et al. |
| 6,250,375 B1 | 6/2001 | Lee et al. |
| 6,256,846 B1 | 7/2001 | Lee |
| 6,257,237 B1 | 7/2001 | Suzuki |
| 6,272,722 B1 | 8/2001 | Lai |
| 6,321,421 B1 | 11/2001 | Lim |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,360,406 B1 * | 3/2002 | Patterson et al. ............... 24/457 |
| 6,374,826 B1 | 4/2002 | Gunaratnam et al. |
| 6,381,813 B1 | 5/2002 | Lai |
| 6,388,640 B1 | 5/2002 | Chigira et al. |
| 6,397,847 B1 | 6/2002 | Scarberry et al. |
| 6,408,853 B1 * | 6/2002 | Chang ........................ 128/857 |
| 6,412,487 B1 | 7/2002 | Gunaratnam et al. |
| 6,418,928 B1 | 7/2002 | Bordewick et al. |
| 6,422,238 B1 | 7/2002 | Lithgow |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,230 B1 | 8/2002 | Gunaratnam et al. |
| 6,449,817 B1 | 9/2002 | Hsu |
| 6,463,931 B1 | 10/2002 | Kwok et al. |
| 6,467,483 B1 | 10/2002 | Kopacko et al. |
| 6,491,034 B1 | 12/2002 | Gunaratnam et al. |
| 6,494,207 B1 | 12/2002 | Kwok |
| D468,823 S | 1/2003 | Smart |
| 6,513,206 B1 | 2/2003 | Banitt et al. |
| 6,513,526 B2 | 2/2003 | Kwok et al. |
| 6,520,182 B1 | 2/2003 | Gunaratnam |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,557,556 B2 | 5/2003 | Kwok et al. |
| 6,561,190 B1 | 5/2003 | Kwok |
| 6,561,191 B1 | 5/2003 | Kwok |
| 6,581,601 B2 | 6/2003 | Ziaee |
| 6,595,214 B1 | 7/2003 | Hecker |
| 6,615,830 B1 | 9/2003 | Serowski et al. |
| 6,615,832 B1 | 9/2003 | Chen |
| 6,615,834 B2 | 9/2003 | Gradon et al. |
| 6,626,177 B1 | 9/2003 | Ziaee |
| 6,631,718 B1 | 10/2003 | Lovell |
| D484,237 S | 12/2003 | Lang et al. |
| 6,675,446 B2 * | 1/2004 | Buettell ........................ 24/122.6 |
| 6,679,260 B2 | 1/2004 | Her |
| 6,679,261 B2 | 1/2004 | Lithgow |
| 6,691,707 B1 | 2/2004 | Gunaratnam et al. |
| 6,691,708 B2 | 2/2004 | Kwok et al. |
| 6,701,535 B2 | 3/2004 | Dobbie et al. |
| 6,701,927 B2 | 3/2004 | Kwok et al. |
| 6,705,647 B1 | 3/2004 | Palmer |

(56) References Cited

U.S. PATENT DOCUMENTS

| | | |
|---|---|---|
| 6,712,072 B1 | 3/2004 | Lang |
| 6,729,333 B2 | 5/2004 | Barnett et al. |
| D492,992 S | 7/2004 | Guney et al. |
| D493,521 S | 7/2004 | Guney |
| 6,789,543 B2 | 9/2004 | Cannon |
| 6,796,308 B2 | 9/2004 | Gunaratnam et al. |
| 6,805,117 B1 | 10/2004 | Ho et al. |
| 6,823,869 B2 | 11/2004 | Raje et al. |
| 6,832,610 B2 | 12/2004 | Gradon et al. |
| 6,832,615 B2 | 12/2004 | Hensel |
| D502,260 S | 2/2005 | Lang et al. |
| 6,851,425 B2 | 2/2005 | Jaffre |
| 6,851,428 B2 | 2/2005 | Dennis |
| 6,860,269 B2 | 3/2005 | Kwok et al. |
| 6,907,882 B2 | 6/2005 | Ging |
| 6,918,390 B2 | 7/2005 | Lithgow et al. |
| 6,926,004 B2 | 8/2005 | Schumacher |
| 6,973,929 B2 | 12/2005 | Gunaratnam |
| 6,986,352 B2 | 1/2006 | Frater et al. |
| D515,698 S | 2/2006 | Lang et al. |
| 6,997,188 B2 | 2/2006 | Kwok et al. |
| 7,000,614 B2 | 2/2006 | Lang et al. |
| 7,005,414 B2 | 2/2006 | Barnikol et al. |
| 7,007,696 B2 | 3/2006 | Palkon et al. |
| 7,011,090 B2 | 3/2006 | Drew et al. |
| 7,021,311 B2 | 4/2006 | Gunaratnam et al. |
| 7,036,508 B2 | 5/2006 | Kwok |
| 7,047,965 B1 | 5/2006 | Ball |
| 7,047,972 B2 | 5/2006 | Ging et al. |
| 7,059,326 B2 | 6/2006 | Heidmann et al. |
| 7,066,179 B2 | 6/2006 | Eaton et al. |
| 7,069,932 B2 | 7/2006 | Eaton et al. |
| 7,089,939 B2 | 8/2006 | Walker et al. |
| 7,095,938 B2 | 8/2006 | Tolstikhin |
| 7,100,610 B2 | 9/2006 | Biener |
| 7,107,989 B2 | 9/2006 | Frater et al. |
| 7,112,179 B2 | 9/2006 | Bonutti et al. |
| 7,178,525 B2 | 2/2007 | Matula, Jr. et al. |
| 7,185,652 B2 | 3/2007 | Gunaratnam et al. |
| 7,207,334 B2 | 4/2007 | Smart |
| 7,207,335 B2 | 4/2007 | Kwok et al. |
| 7,216,647 B2 | 5/2007 | Lang et al. |
| 7,219,670 B2 | 5/2007 | Jones et al. |
| 7,234,466 B2 | 6/2007 | Kwok et al. |
| 7,234,773 B2 | 6/2007 | Raftery et al. |
| 7,290,546 B2 | 11/2007 | Sprinkle et al. |
| 7,296,574 B2 | 11/2007 | Ho et al. |
| 7,318,437 B2 | 1/2008 | Gunaratnam et al. |
| 7,318,439 B2 | 1/2008 | Raje et al. |
| 7,320,323 B2 | 1/2008 | Lang et al. |
| 7,353,826 B2 | 4/2008 | Sleeper et al. |
| 7,353,827 B2 | 4/2008 | Geist |
| 7,406,965 B2 | 8/2008 | Kwok et al. |
| 7,461,656 B2 | 12/2008 | Gunaratnam et al. |
| 7,472,704 B2 | 1/2009 | Gunaratnam |
| 7,487,772 B2 | 2/2009 | Ging et al. |
| 7,487,777 B2 | 2/2009 | Gunaratnam et al. |
| 7,503,327 B2 | 3/2009 | Gunaratnam |
| 7,509,958 B2 | 3/2009 | Amarasinghe et al. |
| 7,523,754 B2 | 4/2009 | Lithgow |
| 7,610,916 B2 | 11/2009 | Kwok et al. |
| 7,614,400 B2 | 11/2009 | Lithgow et al. |
| 7,621,274 B2 | 11/2009 | Sprinkle et al. |
| 7,654,263 B2 | 2/2010 | Lang et al. |
| 7,665,464 B2 | 2/2010 | Kopacko et al. |
| 7,743,767 B2 | 6/2010 | Ging et al. |
| 7,762,259 B2 | 7/2010 | Gunaratnam |
| 7,775,209 B2 | 8/2010 | Biener et al. |
| 7,779,832 B1 | 8/2010 | Ho |
| 7,814,911 B2 | 10/2010 | Bordewick et al. |
| 7,819,119 B2 | 10/2010 | Ho |
| 7,827,987 B2 | 11/2010 | Woodard et al. |
| 7,827,990 B1 | 11/2010 | Melidis et al. |
| 7,841,345 B2 | 11/2010 | Guney et al. |
| 7,856,980 B2 | 12/2010 | Lang et al. |
| 7,856,982 B2 | 12/2010 | Matula, Jr. et al. |
| 7,861,715 B2 | 1/2011 | Jones et al. |
| 7,874,293 B2 | 1/2011 | Gunaratnam et al. |
| 7,878,199 B2 | 2/2011 | Ging et al. |
| 7,882,837 B2 | 2/2011 | Kwok et al. |
| 7,900,635 B2 | 3/2011 | Gunaratnam et al. |
| 7,942,148 B2 | 5/2011 | Davidson et al. |
| 7,942,149 B2 | 5/2011 | Gunaratnam |
| 7,967,013 B2 | 6/2011 | Ging et al. |
| 7,967,014 B2 | 6/2011 | Heidmann et al. |
| 7,971,590 B2 | 7/2011 | Kwok et al. |
| 7,992,559 B2 | 8/2011 | Lang et al. |
| 8,042,538 B2 | 10/2011 | Ging et al. |
| 8,042,546 B2 | 10/2011 | Gunaratnam et al. |
| 8,051,850 B2 | 11/2011 | Kwok et al. |
| 8,091,553 B2 | 1/2012 | Bordewick et al. |
| 8,113,203 B2 | 2/2012 | Lithgow et al. |
| 8,136,524 B2 | 3/2012 | Ging et al. |
| 8,186,348 B2 | 5/2012 | Kwok et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,230,855 B2 | 7/2012 | Raje et al. |
| 2002/0053347 A1 | 5/2002 | Ziaee |
| 2003/0062048 A1 | 4/2003 | Gradon et al. |
| 2003/0075180 A1 | 4/2003 | Raje et al. |
| 2003/0084904 A1 | 5/2003 | Gunaratnam |
| 2003/0089373 A1 | 5/2003 | Gradon et al. |
| 2003/0196656 A1 | 10/2003 | Moore et al. |
| 2004/0094157 A1 | 5/2004 | Dantanarayana et al. |
| 2004/0112385 A1 | 6/2004 | Drew et al. |
| 2004/0112387 A1 | 6/2004 | Lang et al. |
| 2004/0118406 A1 | 6/2004 | Lithgow et al. |
| 2004/0177850 A1 | 9/2004 | Gradon et al. |
| 2004/0211428 A1 | 10/2004 | Jones, Jr. et al. |
| 2004/0216747 A1 | 11/2004 | Jones et al. |
| 2004/0226566 A1 | 11/2004 | Gunaratnam et al. |
| 2005/0011522 A1 | 1/2005 | Ho et al. |
| 2005/0098183 A1 | 5/2005 | Nash et al. |
| 2005/0199239 A1 | 9/2005 | Lang et al. |
| 2005/0211252 A1 | 9/2005 | Lang et al. |
| 2006/0081250 A1 | 4/2006 | Bordewick et al. |
| 2006/0118117 A1 | 6/2006 | Berthon-Jones et al. |
| 2006/0169286 A1 | 8/2006 | Eifler et al. |
| 2006/0219246 A1 | 10/2006 | Dennis |
| 2006/0254593 A1 | 11/2006 | Chang |
| 2006/0283461 A1 | 12/2006 | Lubke et al. |
| 2007/0044804 A1 | 3/2007 | Matula et al. |
| 2007/0137653 A1 | 6/2007 | Wood |
| 2007/0144525 A1 | 6/2007 | Davidson et al. |
| 2008/0178885 A1 | 7/2008 | Raje et al. |
| 2008/0257354 A1 | 10/2008 | Davidson et al. |
| 2008/0264421 A1 | 10/2008 | Kwok et al. |
| 2008/0314389 A1 | 12/2008 | Thomas et al. |
| 2009/0044808 A1 | 2/2009 | Guney |
| 2009/0050156 A1 | 2/2009 | Ng et al. |
| 2009/0126739 A1 | 5/2009 | Ng et al. |
| 2009/0139526 A1 | 6/2009 | Melidis et al. |
| 2009/0173343 A1 | 7/2009 | Omura et al. |
| 2009/0223521 A1 | 9/2009 | Howard et al. |
| 2010/0000543 A1 | 1/2010 | Berthon-Jones et al. |
| 2010/0071700 A2 | 3/2010 | Hitchcock et al. |
| 2010/0089401 A1 | 4/2010 | Lang et al. |
| 2010/0282265 A1 | 11/2010 | Melidis et al. |
| 2010/0300447 A1 | 12/2010 | Biener et al. |
| 2011/0030692 A1 | 2/2011 | Jones et al. |
| 2011/0056498 A1 | 3/2011 | Lang et al. |
| 2011/0094516 A1 | 4/2011 | Chang |
| 2011/0174311 A1 | 7/2011 | Gunaratnam |
| 2011/0226254 A1 | 9/2011 | Lang et al. |
| 2011/0259337 A1 | 10/2011 | Hitchcock et al. |
| 2012/0174928 A1 | 7/2012 | Raje et al. |

FOREIGN PATENT DOCUMENTS

| | | |
|---|---|---|
| AU | 95/16178 | 7/1995 |
| AU | 94/59430 | 10/1995 |
| AU | 95/32914 | 2/1996 |
| AU | 97/41018 | 4/1998 |

(56) References Cited

FOREIGN PATENT DOCUMENTS

| | | |
|---|---|---|
| AU | 98/89312 | 1/1999 |
| AU | 200071882 | 6/2001 |
| CA | 618807 | 4/1961 |
| CA | 623129 | 7/1961 |
| CA | 1039144 | 9/1978 |
| CA | 88122 | 11/1999 |
| CN | 2419188 Y | 2/2001 |
| CN | 1326371 | 12/2001 |
| CN | 2464353 | 12/2001 |
| CN | 1408453 | 4/2003 |
| CN | 1735438 A | 2/2006 |
| CN | 102038996 A | 5/2011 |
| CN | 102038996 B | 3/2013 |
| DE | 284 800 | 11/1913 |
| DE | 459 104 | 4/1928 |
| DE | 701 690 | 1/1941 |
| DE | 923 500 | 2/1955 |
| DE | 30 15 279 | 10/1981 |
| DE | 159396 | 3/1983 |
| DE | 33 45 067 | 6/1984 |
| DE | 37 07 952 | 3/1987 |
| DE | 35 37 507 | 4/1987 |
| DE | 35 39 073 | 5/1987 |
| DE | 40 04 157 | 4/1991 |
| DE | 42 12 259 | 1/1993 |
| DE | 42 33 448 | 4/1993 |
| DE | 43 43 205 | 6/1995 |
| DE | 195 48 380 | 7/1996 |
| DE | 196 03 949 | 8/1997 |
| DE | 29715718 | 10/1997 |
| DE | 197 35 359 | 1/1998 |
| DE | 297 21 766 | 3/1998 |
| DE | 29723101 U1 | 7/1998 |
| DE | 298 10 846 | 8/1998 |
| DE | 4 99 00 269.5 | 1/1999 |
| DE | 198 17 332 | 1/1999 |
| DE | 198 07 961 | 8/1999 |
| DE | 198 08 105 | 9/1999 |
| DE | 299 23 126 | 3/2000 |
| DE | 200 05 346 | 5/2000 |
| DE | 299 23 141 | 5/2000 |
| DE | 200 17 940 U1 | 2/2001 |
| DE | 199 54 517 | 6/2001 |
| DE | 199 62 515 | 7/2001 |
| DE | 100 45 183 A1 | 5/2002 |
| DE | 100 51 891 A1 | 5/2002 |
| DE | 10045183 A1 * | 5/2002 |
| DE | 198 40 760 | 3/2003 |
| DE | 103 31 837 | 1/2005 |
| DE | 103 38 169 | 3/2005 |
| DE | 203 21 882 U1 | 2/2012 |
| EP | 0 054 154 | 6/1982 |
| EP | 0 252 052 | 1/1988 |
| EP | 0 264 772 | 4/1988 |
| EP | 0 334 555 | 9/1989 |
| EP | 0 386 605 | 9/1990 |
| EP | 0 427 474 | 5/1991 |
| EP | 0 462 701 | 12/1991 |
| EP | 0 303 090 B1 | 4/1992 |
| EP | 0 549 299 | 6/1993 |
| EP | 0 602 424 | 6/1994 |
| EP | 0 608 684 | 8/1994 |
| EP | 0 697 225 | 7/1995 |
| EP | 0 178 925 A2 | 4/1996 |
| EP | 0 747 078 | 12/1996 |
| EP | 0 821 978 | 2/1998 |
| EP | 0 853 962 | 7/1998 |
| EP | 0 958 841 | 11/1999 |
| EP | 1 027 905 | 8/2000 |
| EP | 1 057 494 | 12/2000 |
| EP | 1 099 452 | 5/2001 |
| EP | 1 163 923 | 12/2001 |
| EP | 1 205 205 | 5/2002 |
| EP | 1 266 674 A1 | 12/2002 |
| EP | 1 334 742 | 8/2003 |
| EP | 1 356 843 | 10/2003 |
| EP | 1 555 039 | 7/2005 |
| EP | 1 545 673 B1 | 12/2013 |
| ES | 145309 | 1/2000 |
| FR | 780018 | 4/1935 |
| FR | 2 574 657 | 6/1986 |
| FR | 2 658 725 | 8/1991 |
| FR | 2 691 906 | 12/1993 |
| FR | 2 720 280 | 12/1995 |
| FR | 2 749 176 | 12/1997 |
| FR | 99/16 | 8/1999 |
| GB | 649 689 | 1/1951 |
| GB | 823 887 | 11/1959 |
| GB | 1 395 391 | 5/1975 |
| GB | 1 467 828 | 3/1977 |
| GB | 2 145 335 | 3/1985 |
| GB | 2 147 506 | 5/1985 |
| GB | 2 164 569 | 3/1986 |
| GB | 2 186 801 | 8/1987 |
| GB | 2 267 648 | 12/1993 |
| GB | 2080119 | 12/1998 |
| GB | 2080120 | 12/1998 |
| GB | 2080121 | 12/1998 |
| JP | S39-13991 | 7/1964 |
| JP | S48-55696 | 10/1971 |
| JP | S52-76695 | 6/1977 |
| JP | S59-55535 | 4/1984 |
| JP | S61-67747 | 5/1986 |
| JP | H06-184803 | 7/1994 |
| JP | H07-21058 | 4/1995 |
| JP | H07-308381 | 11/1995 |
| JP | H09-501084 | 2/1997 |
| JP | H09-216240 | 8/1997 |
| JP | 9-292588 | 11/1997 |
| JP | H11-000397 | 1/1999 |
| JP | 1105649 | 2/1999 |
| JP | H11-104256 | 4/1999 |
| JP | H11-508159 | 7/1999 |
| JP | H11-381522 | 11/1999 |
| JP | 2000-135103 | 5/2000 |
| JP | 2000-279520 | 10/2000 |
| JP | 2000-325481 | 11/2000 |
| JP | 2000-515784 | 11/2000 |
| JP | 2002-028240 | 1/2002 |
| JP | 2002-543943 | 12/2002 |
| JP | 2003-502119 | 2/2003 |
| JP | 2003-175106 | 6/2003 |
| JP | 2003-190308 | 7/2003 |
| JP | 2004-329941 | 11/2004 |
| JP | 2005-506156 | 3/2005 |
| JP | 3686609 | 8/2005 |
| SE | 65 481 | 8/2000 |
| WO | WO 80/01044 | 5/1980 |
| WO | WO 80/01645 | 8/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 95/04566 | 2/1995 |
| WO | WO 96/17643 | 6/1996 |
| WO | WO 96/25983 | 8/1996 |
| WO | WO 96/39206 | 12/1996 |
| WO | WO 97/00092 | 1/1997 |
| WO | WO 97/07847 | 3/1997 |
| WO | WO 97/09090 | 3/1997 |
| WO | WO 97/41911 | 11/1997 |
| WO | WO 98/04310 | 2/1998 |
| WO | WO 98/11930 | 3/1998 |
| WO | WO 98/12965 | 4/1998 |
| WO | WO 98/18514 | 5/1998 |
| WO | WO 98/24499 | 6/1998 |

(56) References Cited

FOREIGN PATENT DOCUMENTS

| | | |
|---|---|---|
| WO | WO 98/26829 | 6/1998 |
| WO | WO 98/26830 | 6/1998 |
| WO | WO 98/30123 | 7/1998 |
| WO | WO 98/34665 | 8/1998 |
| WO | WO 98/48878 | 11/1998 |
| WO | WO 99/21618 | 5/1999 |
| WO | WO 99/30760 | 6/1999 |
| WO | WO 99/43375 | 9/1999 |
| WO | WO 99/58181 | 11/1999 |
| WO | WO 99/61088 | 12/1999 |
| WO | WO 99/65554 | 12/1999 |
| WO | WO 00/21600 | 4/2000 |
| WO | WO 00/38772 | 7/2000 |
| WO | WO 00/50121 | 8/2000 |
| WO | WO 00/57942 | 10/2000 |
| WO | WO 00/69521 | 11/2000 |
| WO | WO 00/78381 | 12/2000 |
| WO | WO 00/78384 | 12/2000 |
| WO | WO 0078384 A1 * | 12/2000 |
| WO | WO 01/62326 | 8/2001 |
| WO | WO 01/97892 | 12/2001 |
| WO | WO 01/97893 | 12/2001 |
| WO | WO 02/07806 | 1/2002 |
| WO | WO 02/11804 | 2/2002 |
| WO | WO 02/32491 A2 | 4/2002 |
| WO | WO 02/45784 | 6/2002 |
| WO | WO 02/47749 | 6/2002 |
| WO | WO 03/005931 | 1/2003 |
| WO | WO 03/035156 A2 | 5/2003 |
| WO | WO 03/059427 | 7/2003 |
| WO | WO 03/082406 A2 | 10/2003 |
| WO | WO 03/105921 A2 | 12/2003 |
| WO | WO 2004/012803 | 2/2004 |
| WO | WO 2004/021960 | 3/2004 |
| WO | WO 2004/022144 | 3/2004 |
| WO | WO 2004/022145 | 3/2004 |
| WO | WO 2004/022146 | 3/2004 |
| WO | WO 2004/022147 | 3/2004 |
| WO | WO 2004/041342 | 5/2004 |
| WO | WO 2004/073778 | 9/2004 |
| WO | WO 2004/078228 | 9/2004 |
| WO | WO 2004/096332 | 11/2004 |
| WO | WO 2005/002656 | 1/2005 |
| WO | WO 2005/018523 | 3/2005 |
| WO | WO 2005/028010 | 3/2005 |
| WO | WO 2005/063326 | 7/2005 |
| WO | WO 2005/063328 | 7/2005 |
| WO | WO 2005/068002 | 7/2005 |
| WO | WO 2005/094928 | 10/2005 |
| WO | WO 2005/123166 | 12/2005 |
| WO | WO 2006/000046 | 1/2006 |
| WO | WO 2006/074513 | 7/2006 |
| WO | WO 2006/074515 | 7/2006 |
| WO | WO 2006/074516 | 7/2006 |
| WO | WO 2006/138416 | 12/2006 |
| WO | WO 2007/045008 | 4/2007 |
| WO | WO 2007/048174 | 5/2007 |
| WO | WO 2009/026627 | 3/2009 |
| WO | WO 2009/052560 | 4/2009 |
| WO | WO 2009/062265 | 5/2009 |
| WO | WO 2009/108995 | 9/2009 |
| WO | WO 2010/066004 | 6/2010 |

OTHER PUBLICATIONS

Notification of the First Office Action mailed Oct. 26, 2011 in Chinese Appln. No. 201010620187.7, with English translation.
Notification of Acceptance of the Request for Invalidation issued Oct. 8, 2013 in Chinese Patent No. 201010620187.7, with English Translation (5 pages).
Request for the Invalidation of a Patent Right mailed Sep. 13, 2013 in Chinese Patent No. 201010620187.7, with English Translation (56 pages).
Extended European Search Report mailed Nov. 7, 2013 in European Application No. 13152059.5 (6 pages).
Extended European Search Report mailed Nov. 7, 2013 in European Application No. 13152062.9 (6 pages).
Patent Examination Report No. 1 issued Apr. 23, 2013 in Australian Application No. 2012233050 (5 pages).
4 additional photographs of "Weinmann Mask," before applicants' filing date.
9 photographs of Weinmann mask, WM 23122, 1991.
Australian Appln. No. 2005253641—Examiner's First Report, dated Apr. 20, 2010.
Australian Appln. No. 2005253641—Examiner's Report, dated Aug. 18, 2011.
Australian Appln. No. 2005256167—Examiner's First Report, dated Apr. 29, 2010.
Australian Appln. No. 2006206044—Examiner's First Report, dated Dec. 1, 2010.
Australian Appln. No. 2010251884—Examination Report, dated Jul. 27, 2012.
Chinese Appln. No. 200410038106.7—Office Action (w/English translation), dated Jun. 15, 2007.
Chinese Appln. No. 200480011911.9—Office Action (w/English translation), dated Jun. 24, 2010.
Chinese Appln. No. 200480040220.1—Office Action (English translation only), before applicants' filing date.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200580021230.5—Office Action (w/English translation), dated Jul. 3, 2009.
Chinese Appln. No. 200910223650.1—Office Action (w/English translation), dated Mar. 29, 2012.
Chinese Appln. No. 201010508994.X—Office Action (w/ English translation), dated Jun. 15, 2011.
Chinese Appln. No. 201010517066.X—Office Action (w/English translation), dated Nov. 10, 2011.
DeVilbiss Serenity Mask—Instruction Guide 9352 Series, before applicants' filing date.
DeVilbiss Serenity Mask—Mask Accessories, before applicants' filing date.
European Appln. No. EP 02445110.6—Search Report, dated Nov. 6, 2003.
European Appln. No. EP 02714190.2—Search Report, dated Jul. 11, 2006.
European Appln. No. EP 04730413.4—Supplementary Search Report, dated Sep. 29, 2009.
European Appln. No. EP 04802114.1—Supplementary Search Report, dated May 7, 2009.
European Appln. No. EP 05749447.8—Supplementary Search Report, dated Dec. 2, 2009.
European Appln. No. EP 05753870.4—Office Action, dated Jul. 19, 2010.
European Appln. No. EP 05753870.4—Supplementary Search Report, dated Dec. 15, 2009.
European Appln. No. EP 06704773.8—Supplementary Search Report, dated Mar. 29, 2011.
European Appln. No. EP 08161868.8—Search Report, dated Sep. 23, 2008.
European Appln. No. EP 09003544.5—Search Report, dated Jun. 2, 2009.
European Appln. No. EP 09178736.6—Search Report, dated May 6, 2010.
European Appln. No. EP 10166255.9—Search Report, dated Oct. 25, 2010.
European Appln. No. EP 10181516.5—Search Report, dated Jun. 13, 2012.
European Appln. No. EP 10182015.7—Search Report, dated Jun. 15, 2012.
European Appln. No. EP 10185071.7—Search Report, dated Dec. 6, 2010.

(56) References Cited

OTHER PUBLICATIONS

European Appln. No. EP 10185072.5—Search Report, dated Dec. 6, 2010.
European Appln. No. EP 10185073.3—Search Report, dated Dec. 6, 2010.
European Appln. No. EP 12165749.8—Extended Search Report, dated Oct. 18, 2012.
European Appln. No. EP 12165751.4—Extended Search Report, dated Oct. 16, 2012.
German Patent No. 101 51 984—Decision from Opposition hearing by Weinmann (w/English translation), dated Dec. 6, 2007.
Japanese Appln. No. S52-164619—English translation of Figure 1, Dec. 1977.
Japanese Appln. No. 2000-029094—Office Action (English translation only), before applicants' filing date.
Japanese Appln. No. 2001-504444—Office Action (w/English translation only), dated Oct. 26, 2004.
Japanese Appln. No. 2003-537718—Office Action (w/English translation only), dated Oct. 7, 2008.
Japanese Appln. No. 2003-559587—Office Action (w/English translation only), dated Mar. 17, 2009.
Japanese Appln. No. 2004-137431—Office Action (w/English translation), dated Dec. 8, 2009.
Japanese Appln. No. 2005-004072—Office Action (w/English translation), dated Sep. 24, 2009.
Japanese Appln. No. 2006-504029—Office Action (w/English translation), dated Nov. 10, 2009.
Japanese Appln. No. 2006-545843—Office Action (w/English translation), dated Jun. 7, 2011.
Japanese Appln. No. 2007-515732—Office Action (w/English translation), dated Aug. 24, 2010.
Japanese Appln. No. 2007-515732—Office Action (w/English translation), dated Aug. 16, 2011.
Japanese Appln. No. 2007-515732—Office Action (w/English translation), dated Jun. 12, 2012.
Japanese Appln. No. 2007-516895—Office Action (w/English translation), dated Aug. 24, 2010.
Japanese Appln. No. 2007-550640—Office Action (w/English translation), dated Mar. 29, 2011.
Japanese Appln. No. 2007-550640—Office Action (w/English translation), dated Mar. 27, 2012.
Japanese Appln. No. 2008-318985—Office Action (w/English translation), dated Jun. 14, 2011.
Japanese Appln. No. 2010-268127—Office Action (w/English translation), dated Jul. 10, 2012.
Japanese Appln. No. 2011-038110—Office Action (w/English translation), dated Aug. 14, 2012.
Japanese Appln. No. 2011-106504—Office Action (w/English translation), dated Nov. 13, 2012.
Mask 1 Photographs, Respironics Inc., Reusable Full Mask (small) Part #452033 Lot #951108, before applicants' filing date.
Mask 2 Photographs, Puritan—Bennett, Adam Curcuit, Shell Part #231700, Swivel Part #616329-00, Pillows (medium) Part #616324, before applicants' filing date.
Mask 3 Photographs, DeVilbiss Healthcare Inc., Devilbiss Seal-Ring and CPAP Mask Kit (medium), Part #73510-669, before applicants' filing date.
Mask 4 Photographs, Respironics Inc., Monarch Mini Mask with Pressure Port, Part #572004, Monarch Headgear, Part #572011, before applicants' filing date.
Mask 5 Photographs, Healthdyne Technologies, Nasal CPAP Mask (medium narrow), Part #702510, before applicants' filing date.
Mask 6 Photographs, Healthdyne Technologies, Soft Series Nasal CPAP Mask, Part #702020, before applicants' filing date.
Mask 7 Photographs, DeVilbiss Healthcare Inc., Small Mask and Seal Rings, Part #73510-668, before applicants' filing date.
Mask 8 Photographs, Respironics Inc., Reusable Contour Mask (medium), Part #302180, before applicants' filing date.
Mask 9 Photographs, Healthdyne Technologies, Healthdyne Large Headgear, before applicants' filing date.
Mask 10 Photographs, Respironics Inc., Soft Cap (medium), Part #302I42, before applicants' filing date.
Mask 11 Photographs, Weinmann: Hamburg, Nasalmaskensystem mit Schalldämpfer (medium), Part #WN 23105, before applicants' filing date.
Mask 12 Photographs, Life Care, before applicants' filing date.
Mask 13 Photographs, Healthdyne Technologies, before applicants' filing date.
Mark 14 Photographs, King System, before applicants' filing date.
Mask 15 Photographs, Respironics Inc., Pediatric Mask, before applicants' filing date.
Mask 16 Photographs, Hans Rudolph Inc., Hans Rudolph Silicone Rubber Face Mask/8900, before applicants' filing date.
New Zealand Appln. No. 556041—Examination Report, dated May 6, 2011.
New Zealand Appln. No. 564877—Examination Report, dated Dec. 2, 2009.
New Zealand Appln. No. 567375—Examination Report, dated Nov. 17, 2009.
New Zealand Appln. No. 587820—Examination Report, dated Sep. 13, 2010.
New Zealand Appln. No. 592219—Examination Report, dated Apr. 11, 2011.
New Zealand Appln. No. 597689—Examination Report, dated Jan. 25, 2012.
PCT/AU2003/001160—International Search Report, dated Oct. 8, 2003.
PCT/AU2004/000563—International Search Report, dated Jul. 23, 2004.
PCT/AU2004/001760—International Search Report, dated Feb. 3, 2005.
PCT/AU2004/001760—International Preliminary Report on Patentability, dated Jul. 3, 2006.
PCT/AU2004/001813—International Search Report, dated Mar. 7, 2005.
PCT/AU2004/001813—International Preliminary Report on Patentability, dated Jul. 3, 2006.
PCT/AU2005/000850—International Search Report, dated Aug. 12, 2005.
PCT/AU2005/000850—International Preliminary Report on Patentability, dated Dec. 20, 2006.
PCT/AU2005/000931—International Search Report, dated Jul. 19, 2005.
PCT/AU2005/000931—International Preliminary Report on Patentability, dated Dec. 28, 2006.
PCT/AU2006/000037—International Search Report, dated Mar. 17, 2006.
PCT/AU2006/001570—International Search Report, dated Jan. 8, 2007.
PCT/AU2009/000241—International Search Report, dated May 18, 2009.
PCT/AU2009/001102—International Search Report, dated Dec. 11, 2009.
PCT/AU2010/000657—International Search Report, dated Sep. 9, 2010.
PCT/EP2004/012811—International Search Report, dated Apr. 12, 2005.
Photograph of Weinmann Mask, acquired prior to 1998.
Product Brochure for ResMed "Sullivan® Mirage™—The Mirage is Real. A Perfect Fit-First Time," ©1997 ResMed. Limited, 4 pages.
Product Brochure for ResMed "Sullivan® Mirage™—The Mirage is Real. A Perfect Fit-First Time," ©1998 ResMed Limited, 4 pages.
ResCare Limited, "Sullivan™ Nasal CPAP System, Nose Mask Clip—User Instructions" May 1990, 1 page.
ResMed Ltd., "Improving patient compliance with The ResMed Range of Mask Systems the Ultimate Interface for CPAP treatment," 4 pages, before applicants' filing date.
ResMed, Mask Systems Product Brochure, Sep. 1992, 2 pages.
Respironics, Inc., "Nasal Mask System Silicone Contour Mask," Product Instructions, Jun. 1997, 2 pages.
"Somnomask" brochure, 1999, along with various invoices relating to the "Somnomask".

(56) References Cited

OTHER PUBLICATIONS

Somnotron CPAP-Great WM 2300 Instruction Manual, Weinmann Hamburg, 1991, 11 pages.
The ResMed Range of Mask Systems, product brochure, Nov. 1995, 4 pages.
U.S. Appl. No. 12/083,779—Office Action, dated Feb. 17, 2012.
U.S. Appl. No. 12/083,779—Office Action, dated Sep. 28, 2012.
Provisional U.S. Appl. No. 60/227,472, filed Aug. 2000 (expired).
Provisional U.S. Appl. No. 60/424,696, filed Nov. 8, 2002 (expired).
Provisional U.S. Appl. No. 60/467,572, filed May 2003 (expired).
Provisional U.S. Appl. No. 60/643,121, filed Jan. 12, 2005 (expired).
Examiner's First Report Mailed Jun. 22, 2011 in Australian Appln. No. 2010201443 (2 pages).
Notice of Reasons for Rejection mailed Mar. 3, 2009 in Japanese Appln. No. 2004-569777, with English translation.
Supplementary European Search Report mailed Jun. 15, 2010 in European Application No. 03793491.6.
PCT International Search Report dated Oct. 8, 2003.
Cancellation Request dated Feb. 18, 2014 filed in German Utility Model DE 203 21 882, with English Translation (35 pages).
Brief dated Mar. 5, 2014 Requesting a Declaratory Decision filed in German Utility Model DE 203 21 882, with English Translation (3 pages).
Kreisler's Petition dated Mar. 25, 2014 filed in Cancellation Proceedings of German Utility Model DE 203 21 882, with English Translation (8 pages).
Communication of a Notice of Opposition mailed Feb. 17, 2014 in European Patent No. 1 545 673 including a Notice of Opposition dated Feb. 10, 2014, together with an English Translation (36 pages).
Brief Communication mailed Apr. 4, 2014 in European Patent No. 1 545 673 including a Brief dated Mar. 25, 2014, together with an English Translation (9 pages).
Notice of Opposition mailed Feb. 17, 2014 in European Application No. 03793491.6, with English Translation (50 pages).
Office Action dated Nov. 27, 2014 in Chinese Application No. 201310032494.7 with English translation (15 pages).

\* cited by examiner

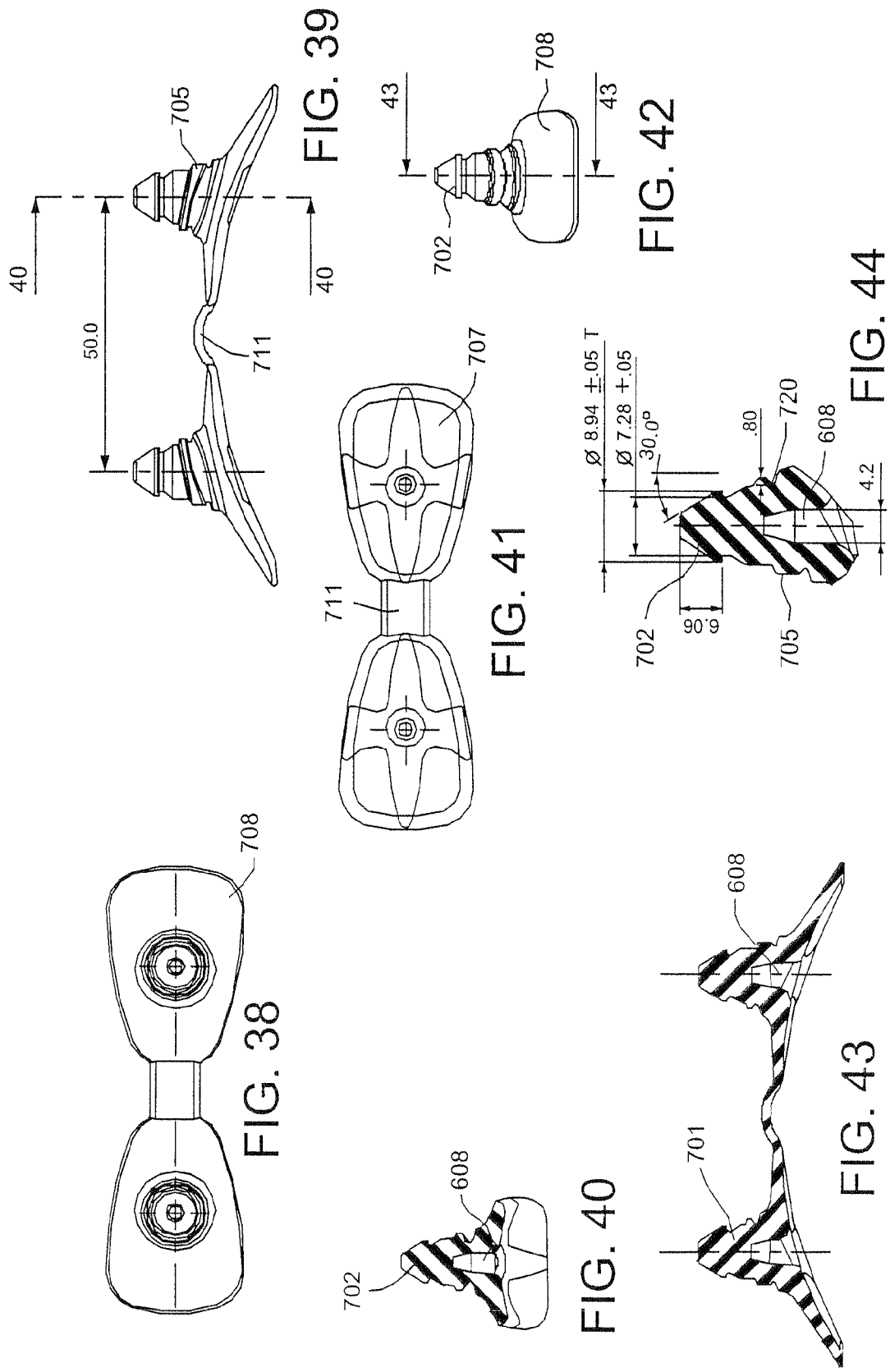

FOREHEAD PAD FOR RESPIRATORY MASK

CROSS-REFERENCE TO RELATED APPLICATIONS

The present application is a divisional of U.S. application Ser. No. 11/705,451, filed Feb. 13, 2007, now allowed, which is a continuation of U.S. application Ser. No. 10/655,595, filed Sep. 5, 2003, now U.S. Pat. No. 7,216,647, which claims the benefit of U.S. Provisional Application Ser. No. 60/424,696 filed Nov. 8, 2002 and U.S. Provisional Application Ser. No. 60/467,572 filed May 5, 2003, and which is a Continuation-In-Part of U.S. Non-Provisional application Ser. No. 10/235,846 filed Sep. 6, 2002, now U.S. Pat. No. 6,823,869, which in turn claims priority to U.S. Provisional Patent Application Ser. No. 60/317,486 filed Sep. 7, 2001 and U.S. Provisional Patent Application Ser. No. 60/342,854 filed Dec. 28, 2001. Each of the above applications is hereby incorporated herein by reference in its entirety.

BACKGROUND OF THE INVENTION

1. Field of the Invention

The invention relates to forehead pads. These pads can be used with a respiratory mask for Non-invasive Positive Pressure Ventilation (NPPV) treatment of Sleep Disordered Breathing (SDB).

2. Background of the Invention

Nasal masks are commonly used in the treatment of respiratory conditions and sleep disorders by delivering a flow of breathable gas to a user to either assist the user in respiration or to provide a therapeutic form of gas to the user to prevent sleep disorders such as obstructive sleep apnea (OSA). These nasal masks typically receive a gas through a supply line, which delivers the gas into a chamber formed by walls of the mask.

The mask is generally semi-rigid and has a face portion that is in communication with the nose and/or mouth of a user. The mask is normally secured to the user's head by straps. The straps are adjusted to pull the mask against the face with sufficient force to achieve a gas-tight seal between the mask and the user's face. Gas is thus delivered to the mask through the aperture to the user's nasal passages and/or mouth.

One of the problems that arises with the use of the mask is that in order for the straps to be tight, the mask is compressed against the user's face and may push unduly hard on the user's nose. Additionally the mask may move around on the user's face. Therefore, masks often contain a forehead support that creates addition contact points between the mask and the user's head. The forehead support minimizes the movement of the mask as well as minimizes uncomfortable pressure points of the mask by preventing the mask from pushing too strongly against the user's nose and/or facial region.

Forehead supports typically have attached thereto a soft comfortable patient-contacting forehead pad. Forehead pads are generally constructed from soft materials, such as silicone, in contrast to the forehead support, which is generally rigid. One form of prior art forehead pad is disclosed in U.S. Pat. No. 6,119,693, the contents of which are hereby incorporated by reference in their entirety.

A problem with existing forehead pads is the mechanism by which the pad is connected to forehead support. The pad must be secured in such a way so as to be easy to insert and remove, but not be unintentionally dislodged. Furthermore, regardless of the relative proximity between the forehead support/pad and the mask frame, there should be no sharp edges against which the user's face can make contact, leading to further discomfort.

One form of known forehead pad is used on the AIR PILOT mask, manufactured by MPV, Truma, Germany, shown in FIGS. 50 to 57. This forehead pad includes a stalk adapted to be pulled through a hole on an arm of a forehead support. The pad also includes two rows of three slots adapted to engage with two rows of three teeth which project rearwardly from the arm of the forehead support. Problems with this type of forehead pad include: (i) it is difficult to assemble; (ii) it is difficult to remove; (iii) it may become dislodged during the night and present sharp teeth to the forehead of a patient; (iv) it has a vague assembly which makes it difficult to know when it is in the correct position; (v) its construction leads to regions of high pressure under the teeth; and (vi) it presents an edge to the forehead of a patient when rocked at an angle.

A further problem with existing forehead pads is that they can lead to uneven pressure on the user's forehead, leading to discomfort and marks on the face. For example, one form of known forehead pad includes a patient contacting surface and a pair of reinforcing struts, as shown in FIGS. 16 to 17. During use, the pad is subject to a compressing force that can lead to pressure points, lines or ridges on the patient contacting surface in the region where the reinforcing struts join it. This can lead to uneven pressure on the user's forehead. The use of existing forehead pads also results in sweating by the user.

Another problem with a known form of forehead support is the mechanism for engaging the forehead pad with the forehead support. The forehead support includes a pair of rigid L-shaped catches c adapted to slidably engage with a recess in the forehead pad, as shown in FIGS. 18 to 20. A problem can arise if a pad is not in position when the forehead support is in use: the catch may abut against the forehead of a user. This can lead to discomfort and marking of the forehead.

Therefore, there exists a need in the art for a forehead pad that overcomes the problems listed above.

SUMMARY OF THE INVENTION

One aspect of the invention is directed towards a mask assembly having a forehead support and a forehead pad that provide more comfort to a user.

Another aspect of the invention is directed towards a forehead pad that distributes contact pressure around the user's forehead.

Another aspect of the invention is directed towards a forehead pad that permits a wide range of motion.

Another aspect of the invention is directed towards a forehead pad that lessens or avoids contact between the user and the edges of the forehead pad.

Another aspect of the invention is directed towards a forehead pad that achieves an even pressure distribution with no localized regions of high forces.

Another aspect of the invention is directed towards providing a forehead pad that is easy to insert in a forehead support and is flexible enough to accommodate a range of different forehead sizes and shapes.

Another aspect of the invention is directed towards a forehead pad that tapers smoothly from the support post to the base region, causing lines of force to be smoothly and evenly carried from the support post to the base region, resulting in an even distribution of the pressure across a user's forehead.

Another aspect of the invention is directed towards a forehead pad for a forehead support of a respiratory mask that comprises a plate region connected to a support post, the support post including a forehead support engaging mechanism.

Another aspect of the invention is directed towards a forehead pad that it is relatively easy to engage with a forehead support but relatively more difficult to disengage.

Another aspect of the invention is directed towards a forehead pad that lessens or avoids contact between the user and the edges of the forehead support.

Another aspect of the invention is directed towards a forehead pad that includes a base portion to contact a user's forehead, a support post comprising a necked down region connected to the base portion, and a head adapted to connect the support post to a forehead support of a respiratory mask.

Another aspect of the invention is directed towards a forehead pad assembly that includes at least two pads, each pad comprising a base portion to contact a user's forehead, a support post comprising a necked down region connected to the base portion, and a head adapted to connect the support post to a forehead support of a respiratory mask. The assembly further comprises at least one connector to connect adjacent base portions.

Other aspects, features and advantages of this invention will become apparent from the following detailed description when taken in conjunction with the accompanying drawings, which are a part of this disclosure and which illustrate, by way of example, principles of preferred embodiments.

BRIEF DESCRIPTION OF FIGURES

FIG. 38 is a rear view of another embodiment a forehead pad according to the present invention;

FIG. 39 is a top view of the embodiment shown in FIG. 38;

FIG. 40 is a cross-sectional view of the embodiment shown in FIG. 38 along axis 40-40;

FIG. 41 is a front view of the embodiment shown in FIG. 38;

FIG. 42 is an end view of the embodiment shown in FIG. 39;

FIG. 43 is a cross-sectional view of the embodiment shown in FIG. 42 along axis 43-43;

FIG. 44 is an expanded cross-sectional view of the embodiment shown in FIG. 42;

DETAILED DESCRIPTION OF ILLUSTRATED EMBODIMENTS

Figure 1:
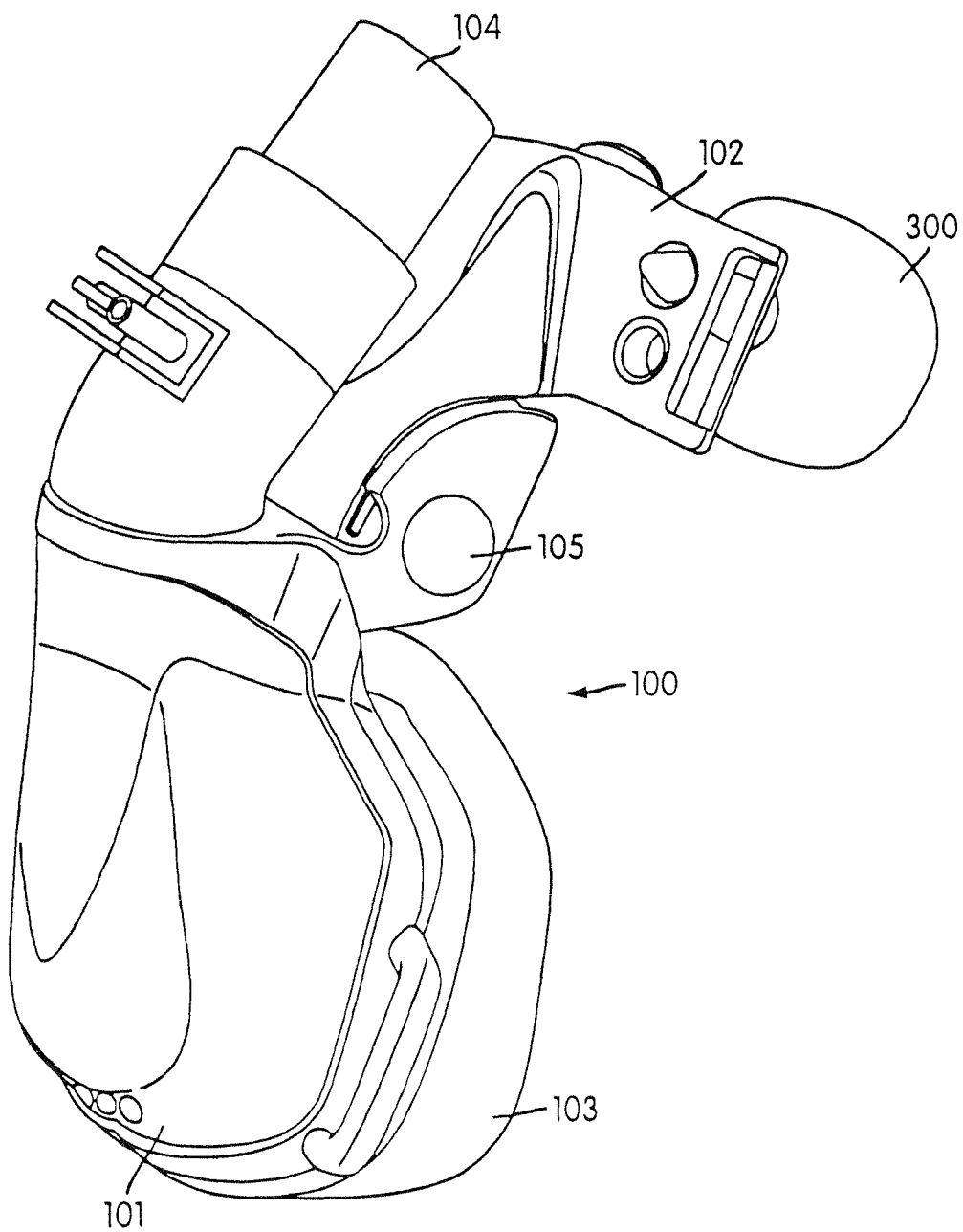
FIG. 1 is a perspective view of a respiratory mask and forehead pad according to one embodiment of the present invention.

FIG. 1 shows an example of a respiratory mask assembly 100. The mask assembly includes a frame portion 101, a forehead support 102, and a forehead pad 300. The mask is adapted to fasten securely and comfortably to a user's face. In particular, the mask assembly 100 comprises a seal-forming region 103 that covers the user's nose and/or mouth and a contains opening 104 to which an air delivery tube can be attached. Air or oxygen flows through the opening 104 under positive pressure.

The forehead support 102 is advantageously connected to the frame portion 101 of the mask assembly 100, e.g., by a pivot device 105, which can be adjusted to allow the forehead support 102 to the accommodate the configuration of a user's face. The forehead support 102 is preferably made from a thermoplastic material. One embodiment of a forehead support is shown in greater detail in FIG. 2.

Figure 2:
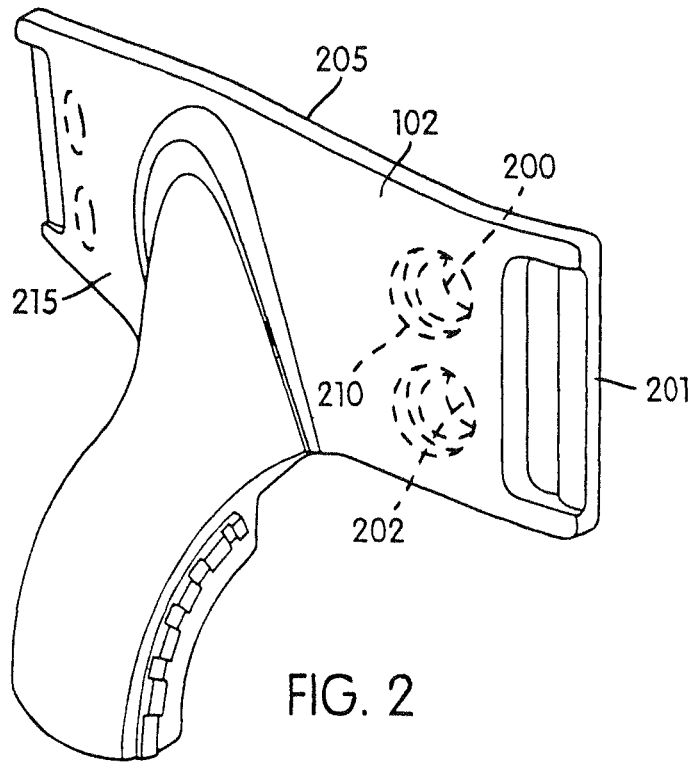
FIG. 2 is a perspective and enlarged view of the forehead support shown in FIG. 1, without the mask frame and pads.

The forehead support 102 can be configured to be essentially straight or it can be curved. The essential straight embodiment is shown in FIG. 2. In the case where the forehead support is curved, the curvature generally follows the curvature of the user's forehead. While this is the most likely structure, it is within the scope of the present invention to use a forehead support 102 that has the opposite curvature, or any combination thereof.

The forehead support 102 can be provided with one or more openings. These openings can be adapted to serve numerous purposes including points of connection to the mask frame, points of connection to any another support surface, points of connection 201 for straps to secure the mask to the user, and apertures 202 for a forehead pad.

In a preferred embodiment of the forehead support 102, the apertures 202 are designed to receive a head of the forehead pad 300. The apertures 202 can be disposed about the forehead support 102 in a manner to allow a user to adjust the position of the forehead pad 300. The apertures 202 are also designed to allow a user to attach the forehead pad 300 securely to the forehead support 102. In a preferred embodiment, the apertures 202 designed to allow a user to attach the forehead pad 300 securely and reversibly to the forehead support 102.

Figure 3:
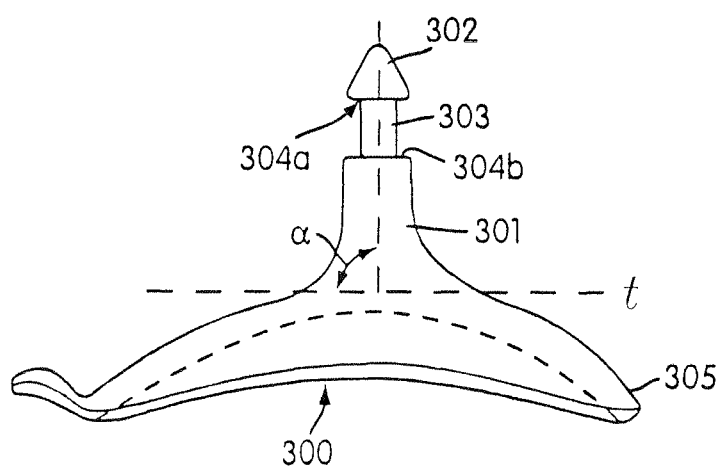
FIG. 3 is a perspective view of one embodiment of a forehead pad according to the present invention.

The forehead pad 300 in accordance with a first embodiment of the invention is shown in greater detail in FIG. 3. The forehead pad 300 comprises a base portion 305 to contact a user's forehead, a support post 301 connected to the base portion, and a head 302 adapted to be connected to the forehead support 102. In this embodiment, the head 302 is bullet or cone shaped, or otherwise tapered. However, other shapes are possible as long as they serve the purpose of the invention.

The base portion 305, support post 301, and head 302 can be separate pieces, designed to fit with each other. In one embodiment, the base portion 305 and the support post 301 can be constructed as one piece. In another embodiment, the support post 301 and the head 302 can be constructed as one piece. In yet another embodiment, the base portion 305 and the head 302 can be constructed without a support post 301. Finally, in a preferred embodiment, the base portion 305, the support post 301, and the head 302 are molded integrally into one piece.

The embodiment shown in FIG. 3 contains a necked down region 303 between the base of the head 302 and the top of the support post 301. In a preferred configuration, the forehead pad is adapted to releasably engage with the forehead support 102. The function of the necked down region 303 is to facilitate this feature. The necked down region 303 is such that its diameter is smaller than the diameter of the base of the head 302. This results in a lip 304a between the base of the head 302 and the necked down region 303 and another lip 304b between the necked down region 303 and the support post 301.

In a preferred embodiment, the necked down region 303 is at least as long as the length of the aperture 202 (FIG. 2) in the forehead support 102. Insertion of the pad 300 through a first end 200 of the aperture in the forehead support 102 results in the head 302 passing through the aperture 202 and emerging out a second end 210. The support post 301 remains on the side of the first end 200 of the aperture 202 with the necked down region 303 occupying at least the length of the aperture. This feature results in easy insertion and a tight fit.

Typically, this insertion can be carried out by a user by applying axial pressure to the base portion 305 of the pad 300. While the support post 301 is flexible, it can withstand the forces needed for assembly. Using the forehead pad embodiment described in FIG. 3 and the forehead support described in FIG. 2 as examples, the head 302, as well as the lip 304a distort as axial force is applied against the first end 200 of the aperture 202, until the head 302 and the lip 304a reach a second end 210 of the aperture 202, whereupon the lip 304a re-expands to engage a first surface 215 of the forehead support 102 adjacent to the aperture 202. Further, the lip 304b abuts against a second surface 205 of the forehead support 102, to prevent axial movement of the pad 300.

The removal of the pad occurs by applying a pulling force it in a direction opposite to the axial force applied for insertion. Once again, the head 302 and the lip 304a distort as the lip 304a disengages with the first surface 215 of the forehead support 102 adjacent to the aperture 202. Lip 304a disengages with the second surface 205 of the forehead support 102. Both the head 302 and the lip 304a regain their original shape after disengagement from the forehead support 200.

The pressure can be applied by a user's fingers and the successful insertion of the pad 300 is indicated not only by the emergence of the head 302 through the first surface 215 of the aperture 202 but typically also by a clicking sound. The combination of sight, sound, and ease of insertion is useful for aged or otherwise infirm users with limited manual and/or digital dexterity. The sound produced has the added benefit of providing the user of knowledge that the pad 300 has been successfully inserted in the dark. This feature can be of importance due to the fact that the masks are used at night. Both the forehead support 102 and the forehead pad 300 are configured such that the pad 300 can be placed in different positions on the support 102 so as to achieve different positions of contact on the user's forehead.

A wide variety of methods well known to a person skilled in the art for the manufacture of the base portion, support post, and head. A preferred method of manufacture is by injection molding.

The support post 301 can project from the base portion 305 at an angle α, defined between a tangent t to the outer surface of the base portion 305 at a point of contact between the support post 301 and the base portion 305. This angle α can be about 90°, i.e., the support post 301 extends essentially straight out from the base portion 305. FIG. 3 shows an embodiment of a forehead pad 300 in which the angle α is about 90°.

Figure 4:
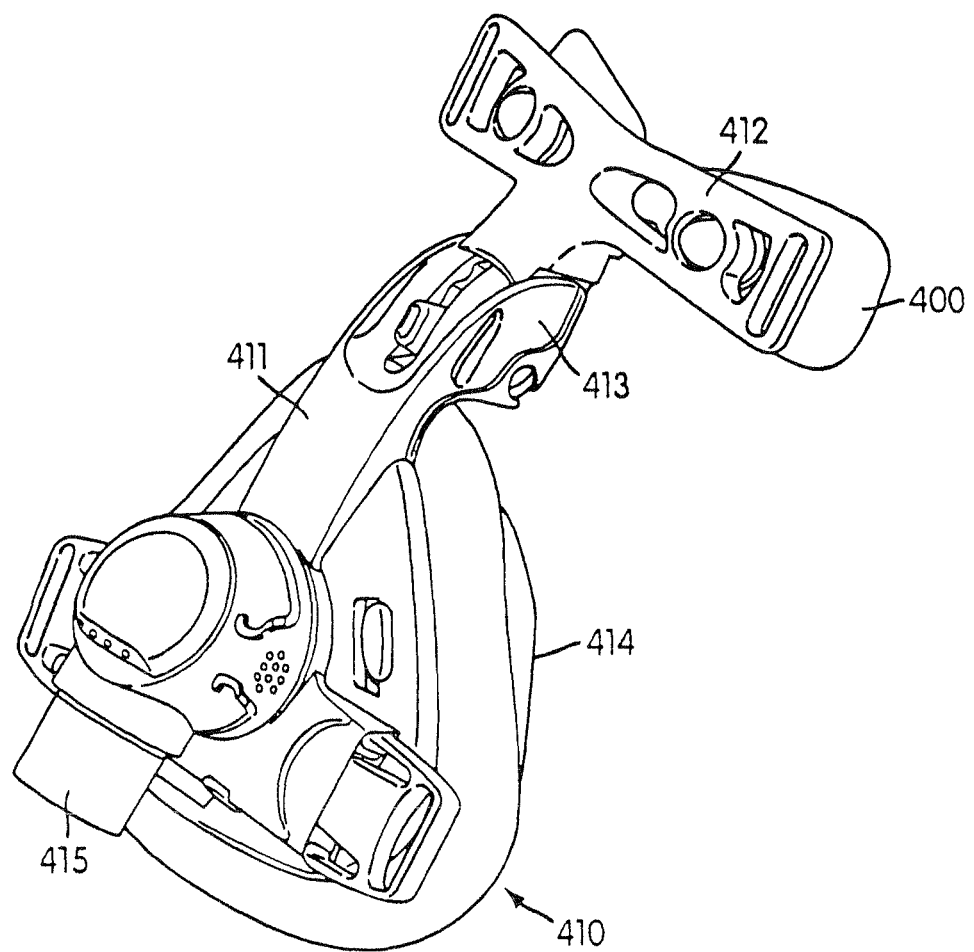
FIG. 4 is a perspective view of a respiratory mask and forehead pad according to one second embodiment of the present invention.

FIG. 4 shows another embodiment of a respiratory mask assembly 410. The mask assembly 410 includes of a frame portion 411, a forehead support 412, and another embodiment of a forehead pad 400. The forehead support 412 is advantageously connected to the frame portion 411 of the mask 410, e.g., by a pivot device 413. The mask assembly 410 comprises a seal-forming cushion 414 that covers a user's nose and/or mouth and contains a swivel elbow 415. The swivel elbow 415 is adapted to receive a supply of air or oxygen flows at positive pressure.

Figure 5:
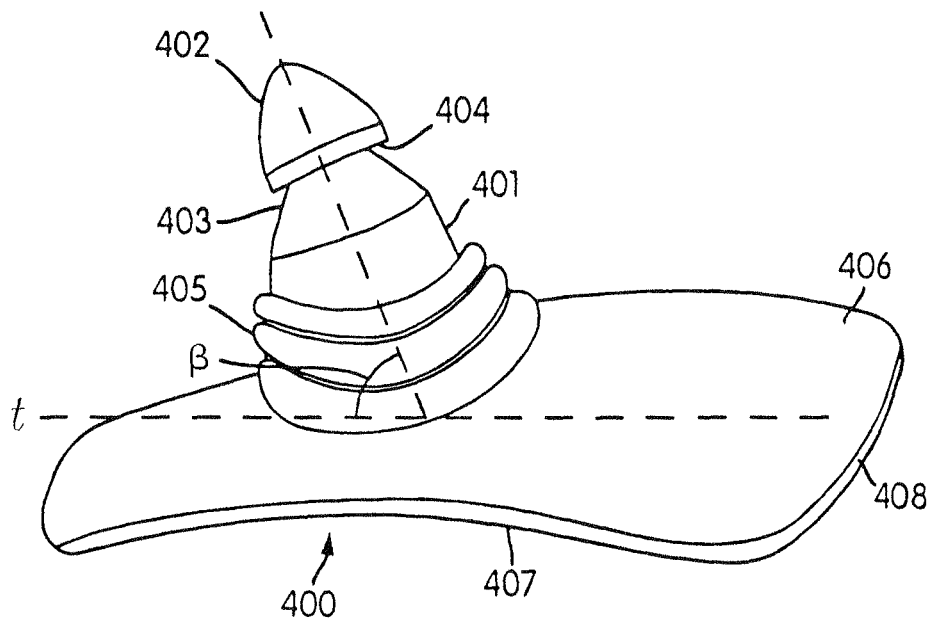
FIG. 5 is a perspective view of another embodiment of a forehead pad according to the present invention.
Figure 6:
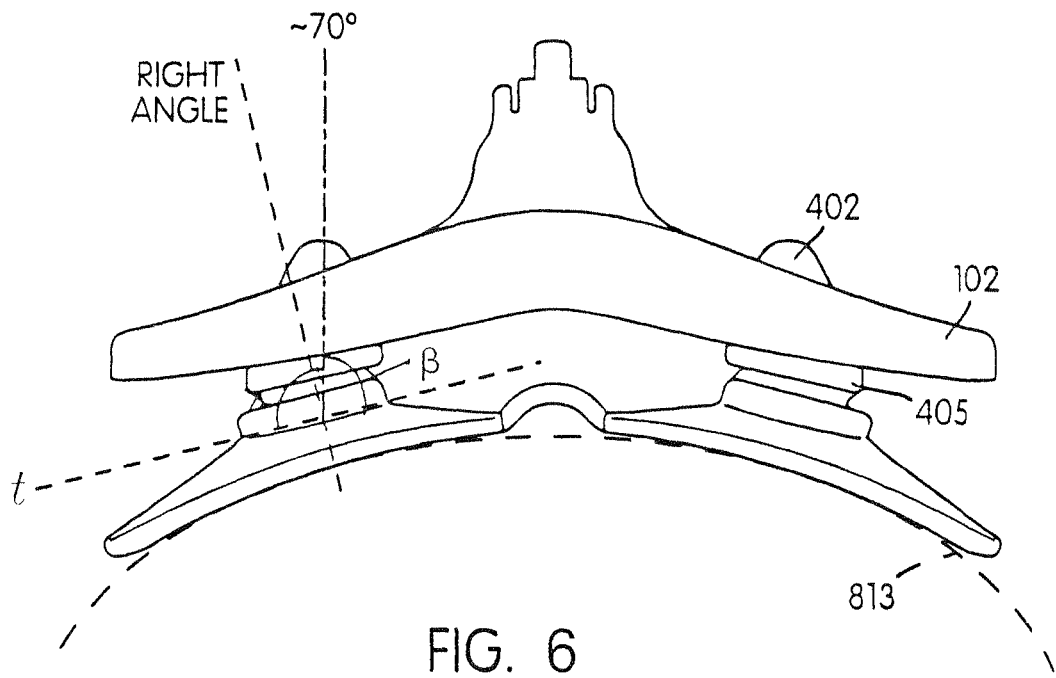
FIG. 6 is a top view of a forehead support including a pair of forehead pads and a forehead of a user.

FIG. 5 shows another embodiment of a forehead pad 400 in greater detail. This embodiment of the pad 400 includes a base portion 408, a support post 401, and a head 402. The general construction and operation is similar to that of the first embodiment although there are several differences in the construction, for example, the angle β between the tangent t to the outer surface of the base portion 406 at a point of contact between the support post 401 and the base portion 408 is between about 60° and about 120°. Preferably, the angle β is about 70°. One advantage of a support post 401 projecting at an angle less than 90° is to allow the base portion 400 to better fit the contours of a user's forehead, as shown in FIG. 6.

The support post 401 can be constructed in a manner so as to make it more flexible. For example, the support post 401 includes cut away portions 405. These cut away portions help the support post to be able to be bent or flexed, varying the angle β in use. In this way, a support post 401 of larger diameter may be used while still retaining a degree of flexibility as shown in FIGS. 68 to 71.

Figure 58:
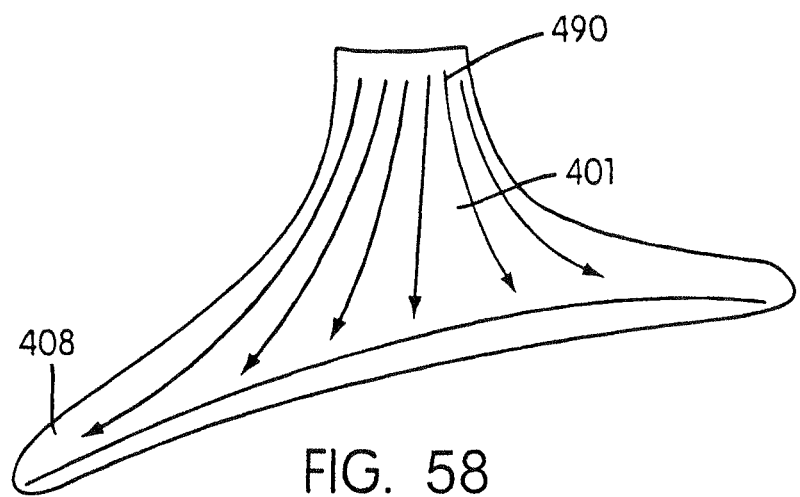
FIG. 58 is a top view of another embodiment of a forehead pad according to the present invention.
Figure 59:
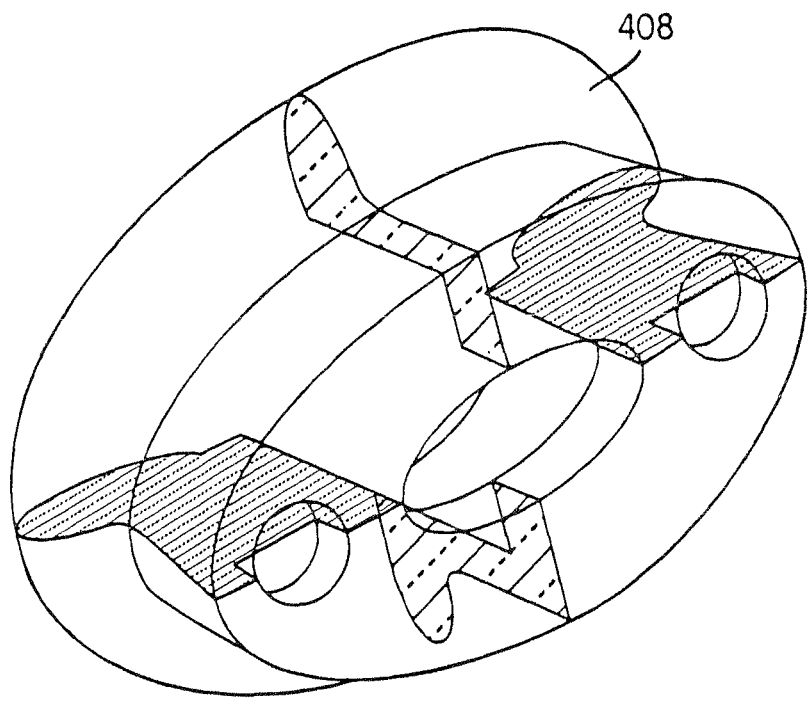
FIG. 59 is a front perspective view of another embodiment of a forehead pad according to the present invention.
Figure 60:
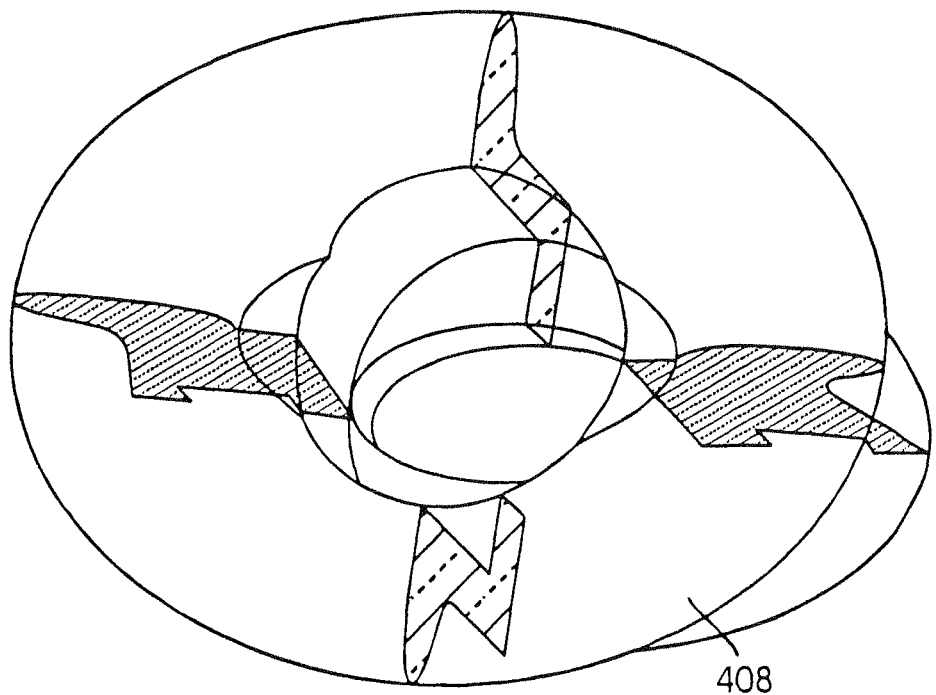
FIG. 60 is a rear perspective view of the forehead pad shown in FIG. 59.
Figure 61:
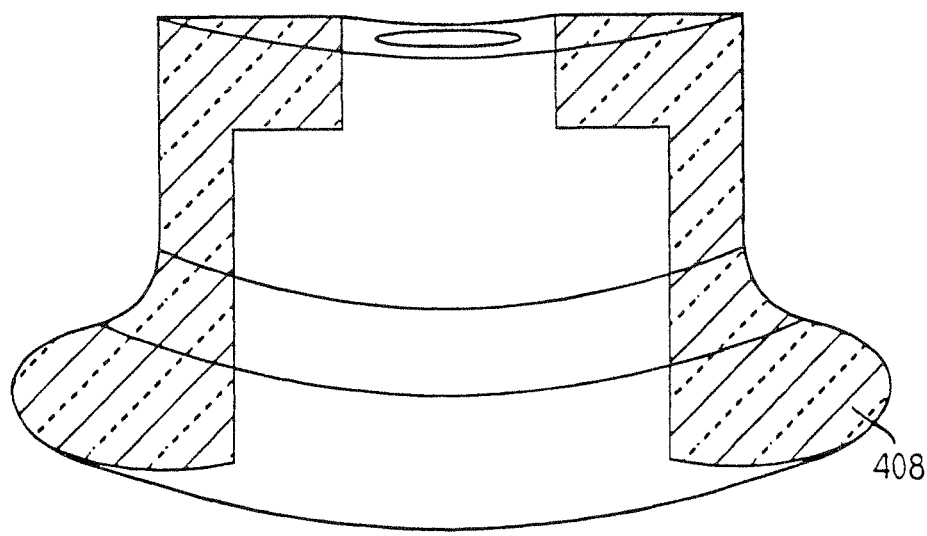
FIG. 61 is a cross-sectional view of the forehead pad shown in FIG. 59 along the minor axis.
Figure 62:
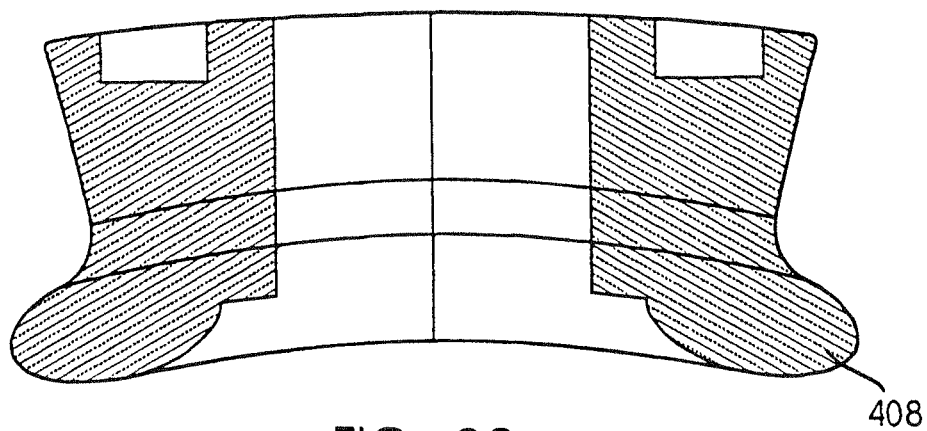
FIG. 62 is a cross-sectional view of the forehead pad shown in FIG. 59 along the major axis.

The base portion 408 can be of any shape, preferably in a pad-like configuration. In one embodiment, a contact region 407 of the base portion 408 is shaped so that the transmission of contact forces to the surface of the forehead of the user takes place under physiologically compatible pressures, as shown in FIG. 58. In a preferred embodiment, the contact region 407 is concavely curved to follow the curvature of a forehead.

Figure 7:
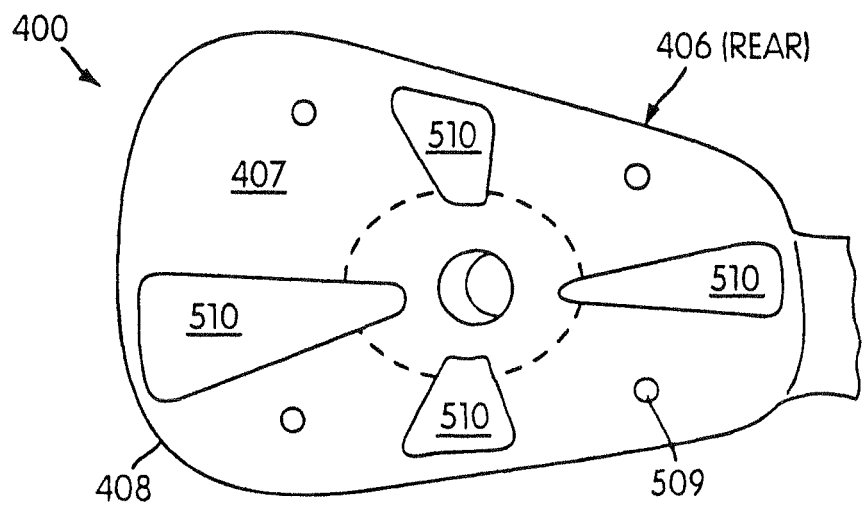
FIG. 7 is a perspective view of the contact surface of one embodiment of a forehead pad showing raised surfaces.

The contact region 407 can optionally include a raised surface pattern 510 as shown in FIG. 7. The pattern 510 reduces the possibility of a suction effect of the pad 400 thereby reducing the drawing of blood in the region and making the pad 400 more comfortable. The raised pattern 510 has the added benefit of reducing sweating. In another embodiment, a rear surface of the pad 400 is given a sandblasted finish to improve ventilation and reduce the likelihood of sweating.

Figure 8:
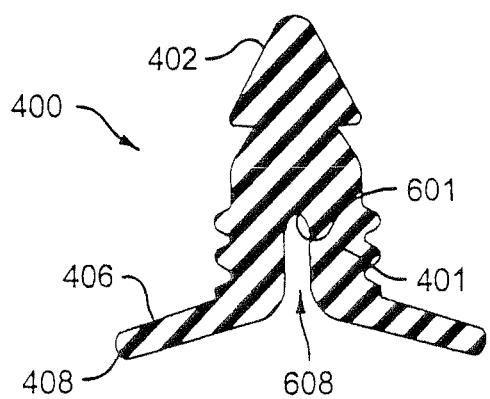
FIG. 8 is a cross-sectional view of one embodiment of a forehead pad showing a hollowed out region.

The base portion 408 and support post 401 of the pad 400 can also include a hollowed out region 608 extending a predetermined distance 601 into the base portion 408 and/or the support post 401 as shown in the cross-sectional view in FIG. 8. In the embodiment shown, the hollowed out region 608 extends through the base portion 408 and partly into the support post 401. This structure imparts a degree of springiness and flexibility to the forehead pad 400. Due to the essentially incompressible nature of silicone, some cut-away regions 405 assist flexibility. The use of the hollowed out region 608 allows for some movement along an axis through the support post 401.

Increasing the diameter of the support post 401 makes the forehead pad 400 easier to insert into the forehead support 102. Furthermore, a larger diameter reduces the likelihood of localized pressure points. However, as the support post 401 is made thicker, it becomes less flexible. Hence the preferred embodiment of the invention balances ease of insertion with flexibility.

In another embodiment, the hollowed out region 608 extends through the base portion 408, the support post 401, and the head 402 resulting in a through-bore 509 (shown in FIG. 7). The through-bore 509 may further facilitate compression of the support post 401 and head 402 during assembly and disassembly. This structure allows a flow of air and/or moisture to occur from the user's skin to the atmosphere, resulting in a reduction of sweating and a more comfortable pad 400.

Figure 9:
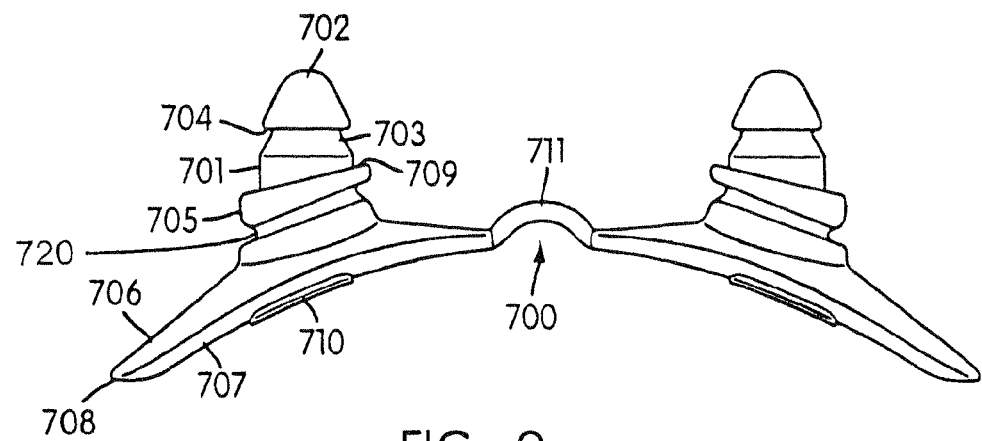
FIG. 9 is a top view of an embodiment of a forehead pad assembly showing two pads joined by a flexible connector.

The support post 401 has a diameter that is in its broadest aspect between about 0.1 cm and about 3.0 cm. More specifically the diameter of the support post of the embodiment of FIG. 9 is between about 0.5 cm and about 1.25 cm, and most preferably the diameter is about 1 cm. The term "about" is meant to indicate that the diameters are not absolute and can be deviated by one skilled in the art. Alternative embodiments, such as those shown in FIGS. 21 to 31 have different diameters.

Figure 37:
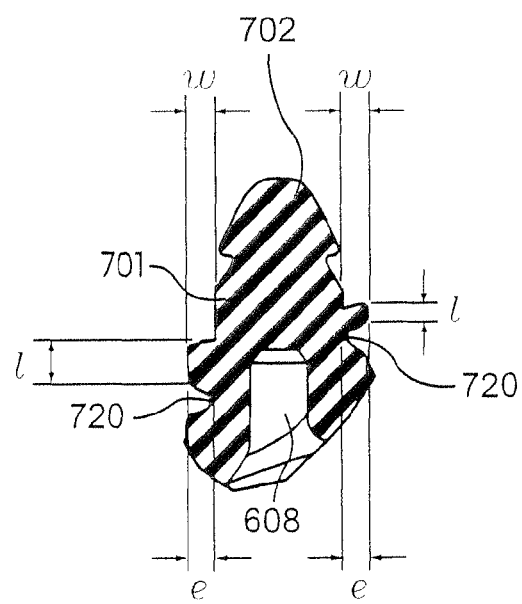
FIG. 37 is a an expanded cross-sectional view of the embodiment shown in FIG. 35.

The support post 401 has a length that is in its broadest aspect between about 0.1 cm and about 2.5 cm. More specifically the length is between about 0.5 cm and about 1.25 cm, and most preferably the length is about 1 cm. Dimensions for one form of forehead pad are shown in FIG. 37. Once again, the term "about" is meant to indicate that the lengths are not absolute and can be deviated by one skilled in the art.

The support post 401 can be straight or it can taper. An example of a straight support post is shown in the embodiment in FIG. 3. The taper can also be such that the region at the base portion is thicker than the head region, as shown in the embodiment in FIG. 5.

As would be understood by one skilled in the art, a wide variety of materials can be used to manufacture the forehead pad in accordance with the present invention. Features of any material used should include biocompatibility, flexibility and comfort. Some examples of such materials include rubber and flexible plastics. In a preferred embodiment, the pad is constructed from cured Liquid Silicone Rubber (Part#2666031, Silastic 94-595-HC) manufactured by Dow Corning, alternatively a silicone with a hardness of approximately 35-45 Shore A may be used. These examples are merely intended to be illustrative and are not limiting in any manner.

In accordance with a preferred embodiment of the present invention, at least two base pads can be joined in a forehead pad assembly 700. In this embodiment, two versions of which are shown in FIGS. 9 and 32 to 44, a connector 711 is used to connect adjacent base portions 708. Any type of connector can be used such as a strap or a flexible bridge portion. An advantage of a connector is that the assembly 700 has a one-piece design which is less likely to be lost. The plurality of base portions 708, with contact regions 707, and connectors 711 can be integrally formed with each other.

As mentioned earlier, the hollowed out region 608 can extend a pre-determined distance into the base portion 708 and/or the support post 701. This distance can be adjusted to increase flexibility of the forehead pad assembly 700. For example, the hollowed out region 608 extends a longer distance into the support post 701 in the embodiment shown in FIG. 44 when compared to the embodiment shown in FIG. 37. Increasing the distance of the hollowed out region 608 has several advantages including flexibility, minimization of contact with the edges of the base portion 708, and better airflow resulting in a reduction in sweating by the user.

The hollowed out region 608 can also have a variety of shapes including conical, pyramidal, cylindrical, or combinations thereof. It is within the scope of this invention that the hollowed out region 608 have additional sub-structures within it including ridges, bumps, or holes.

Figure 10:
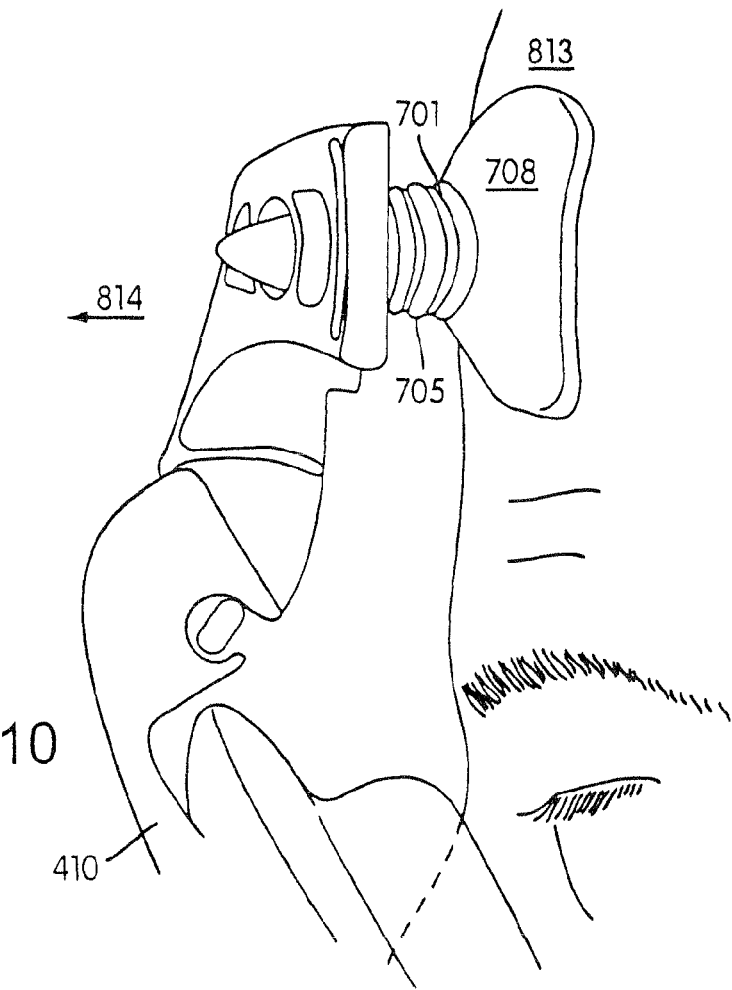
FIG. 10 is a right side view of one embodiment of a forehead pad in a respiratory mask showing contact with a user.

In a preferred embodiment, the two base portions 708 of a forehead pad assembly 700 are adapted in order to be situated above left and right eyebrows of the user. As shown in FIG. 10, a base portion 708 is shown against the user's forehead 813. The support post 701 is designed to act as a spring along the direction of arrow 814. The cut away portions 705 improve its flexibility while maintaining ease of insertion. Another advantage of this design is that it can better accommodate rolling and twisting of the mask 410. A further advantage of the support post 701 is that its diameter is optimized to reduce the effect of a single point of pressure on the forehead 813.

The cut away portions 705 define an undercut 720 between the cut away portions 705 and the base portion 708. The undercut 720 can be a variety of shapes including curved, square, conical, triangular, or any combinations thereof. The undercut 720 depth e can also be varied. The depth e can range between about 0.25 mm to about 1.25 mm, preferably between about 0.5 mm and about 1 mm, and most preferably about 0.75 mm. The term "about" is meant to indicate that the widths and lengths are not absolute and can be deviated by one skilled in the art.

The number, shape, and size, width w, and length l of the cut away portions 705 can be varied to serve a variety of purposes including ease of insertion, ease of removal, flexibility of motion when unassembled with the forehead support, flexibility of motion when assembled with the forehead support, minimization of contact between the user and the edges of the base portion 708, minimization of contact between the user and the edges of the forehead support 102, and angles between the forehead pad assembly 700 and the forehead support 102. The width w can range between about 0.25 mm to about 1.25 mm, preferably between about 0.5 mm and about 1 mm, and most preferably about 0.75 mm. The length l can range between about 0.05 mm to about 1.5 mm, preferably between about 0.25 mm and about 1 mm. Once again, the term "about" is meant to indicate that the widths and lengths are not absolute and can be deviated by one skilled in the art.

The cut away portions 705 can have regions of similar or different widths w and similar or different lengths l. Comparison of the embodiment of the forehead pad assembly 700 shown in FIGS. 32 to 37 with the embodiment of the forehead pad assembly 700 shown in FIGS. 38 to 44 shows a few variations in the cut away portions 705. The width w of the cut away portions 705 in the embodiment shown in FIGS. 38 to 44 is less than the width w of the cut away portions 705 in the embodiment shown in FIGS. 32 to 37.

The undercut 720 in FIG. 40 (a cross-sectional view along line 40-40 of FIG. 39) may be more pronounced than the embodiment of FIGS. 32 to 37. Thus the range of movement of the pad in the vertical plane can be increased, thereby increasing the range of users the mask will fit. In addition, the increased range of movement can help prevent the edge of the pad from coming in contact with the user's forehead, thereby increasing user compliance and comfort. Finally, the increased undercut 720, along with the shape and size of the surrounding cut away portions 705, can effect the force necessary to flex the base portion 708 with respect to the support post 701, thereby optimizing the desired flexing forces within levels acceptable to the user while still allowing adequate performance of the forehead pad assembly 700.

Figure 45:
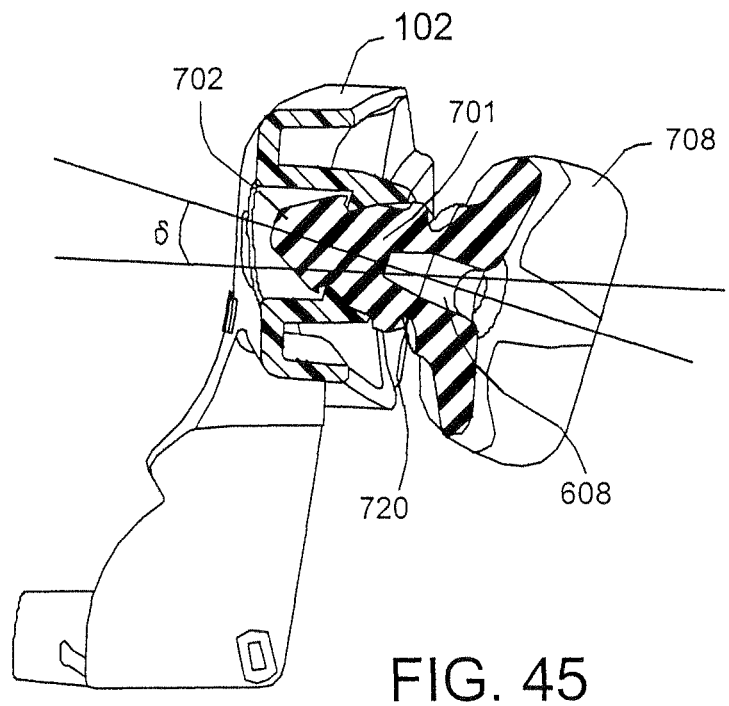
FIG. 45 is a cross-sectional view of one embodiment of a forehead pad engaged with one embodiment of a forehead support according to the present invention.
Figure 46:
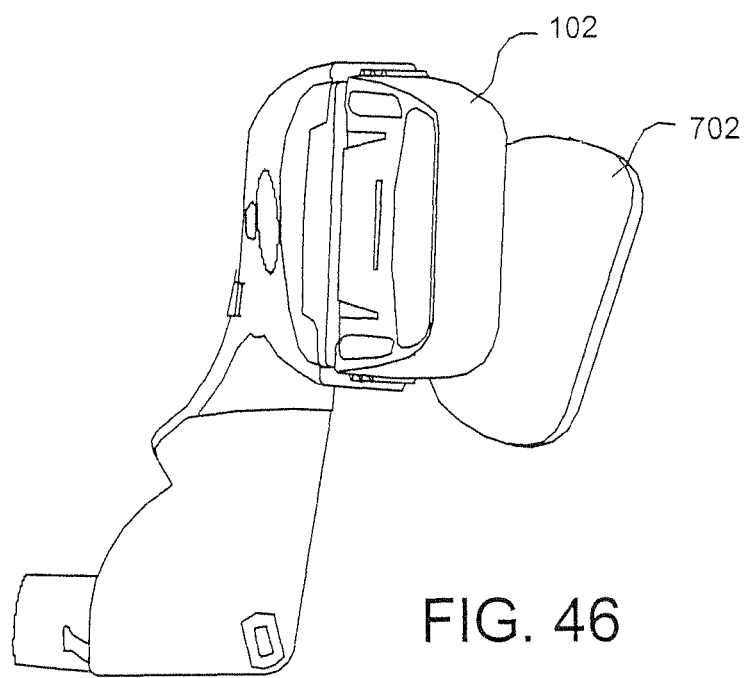
FIG. 46 is side view of the embodiment shown in FIG. 45.

One advantage of reducing the width w and/or increasing the depth e is to vary the angle δ between the forehead pad assembly 700 and the forehead support 102, which in turn allows for greater range of motion and user comfort. The angle δ is the angle between a horizontal line h and a line passing through the center of the base portion 708 and the support post 701. FIGS. 45 and 46 show the embodiment of the forehead pad assembly 700 shown in FIGS. 38 to 44 assembled with the forehead support 102. The angle δ is about 25°. The angle δ of the embodiment of the forehead pad assembly 700 shown in FIGS. 32 to 37 assembled with the forehead support 102 is about 0°. Once again, the term "about" is meant to indicate that the angles are not absolute and can be deviated by one skilled in the art.

Presentation of the base portion 708 of the forehead pad assembly 700 at an angle which is generally parallel to the users forehead provides improved comfort to the user, reducing the likelihood of pressure sores which may result from an uneven presentation. In some forms of long masks, for example a full face mask, the forehead support 102 may be positioned in use higher up the forehead of the user than in a nasal mask.

In the embodiment of forehead support shown in FIG. 42, the support post 701 and base portion 708 are generally perpendicular to one another when viewed from an end. However, in other embodiments, they may be constructed at different angles. For a long mask, because of the curvature of the skull, in order that the base portion 708 of the forehead pad assembly 700 be presented generally parallel to the user's forehead, either (i) the forehead support 102 should be adapted to retain a perpendicular forehead pad assembly 700 at an angle, as shown in FIG. 45, or (ii) the forehead support 102 should be adapted to retain a non-perpendicular forehead pad assembly 700 at a right angle. In the preferred embodiment, a perpendicular pad is used and the forehead support 102 is adapted to retain and present the pad to the forehead of the user at the appropriate angle. In this way, the same forehead pad assembly 700 can be used across a range of mask systems, for example, nasal masks and full face masks, providing an economic benefit to the manufacturer through the use of common parts.

Figure 11:
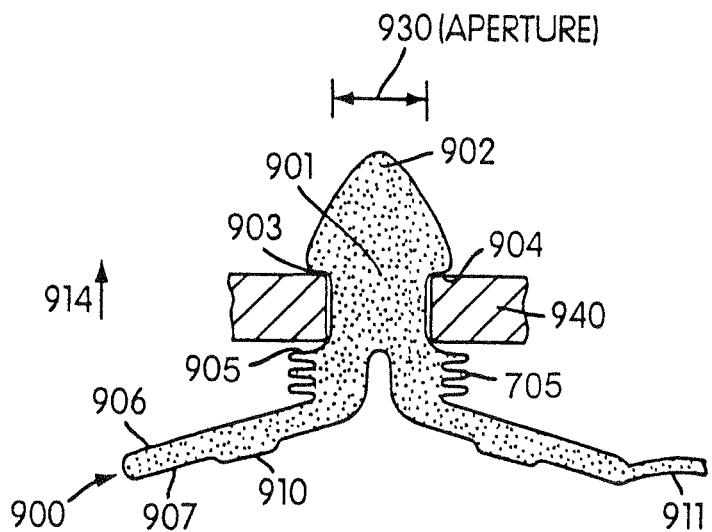
FIG. 11 is a cross-sectional view of one embodiment of a forehead pad engaged with one embodiment of a forehead support.

FIG. 11 shows a cross section of an embodiment of a forehead pad 900 inserted into an aperture 930 in a forehead support 940. To insert the pad 900, axial force is applied in the direction of arrow 914. The head 902 and the lip 904 distort as they pass through the aperture 930. Once the head 902 and the lip 904 are through the aperture 930, the necked down region 903 of the support post 901 occupies the length of the aperture 930. This results in the lip 905 also making contact with the forehead support 940. The engagement of lips 904 and 905 with respective side surfaces of the forehead support 940 results in maintaining the pad 900 in position.

To remove the pad 900 from the forehead support 940 the pad 900 is pulled in an opposite direction to arrow 914. Once again, the head 902 and/or the lip 904 distort as they pass through the aperture 930 enable the pad 900 to disengage from the forehead support 940.

Figure 12:
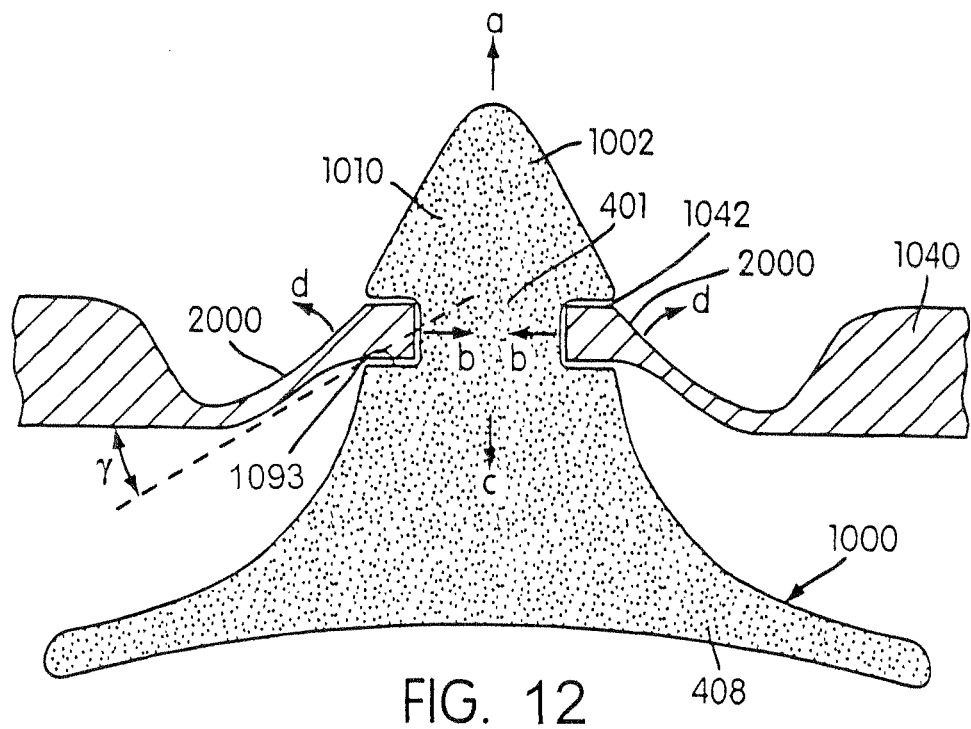
FIG. 12 is a cross-sectional view of another embodiment of a forehead pad engaged with another embodiment of a forehead support.

FIG. 12 shows a cross section of an embodiment of a forehead pad 1000 inserted into another embodiment of a forehead support 1040. The forehead support 1040 has arms 2000 that can move in direction d when pressure is applied to the pad 408 in direction a. In one embodiment, the movement of arms 2000 results in a plastic deformation, i.e., the removal of the pad 408 results in the arms 2000 remaining essentially in the position they were when the pad 408 was inserted. In another embodiment, the movement of arms 2000 results in an elastic deformation, i.e., the removal of the pad 408 results in the arms 2000 returning essentially to the position they were before the pad 408 was inserted. The support post 401 can compress in direction b allowing for ease in insertion and removal but still providing a firm fit. Once inserted, the pad 408 can be adjusted by angle γ.

Figure 13:
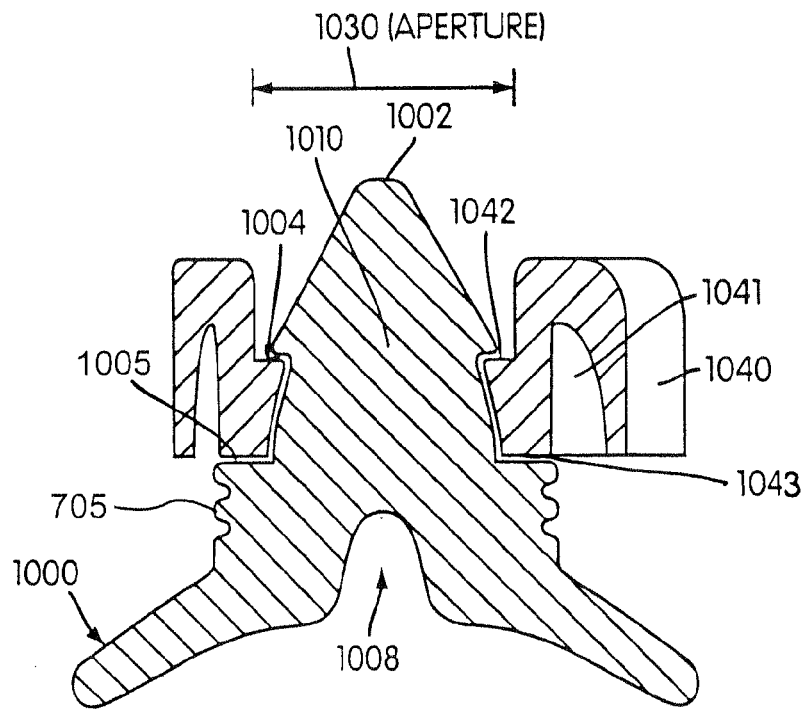
FIG. 13 is a cross-sectional view of another embodiment of a forehead pad engaged with another embodiment of a forehead support.

A cross section of another embodiment of a forehead pad 1000 engaged with a rigid forehead support 1040 is shown in FIG. 13. The forehead support 1040 comprises lips 1042 and 1043. Lip 1042 of the forehead support 1040 is adapted to engage lip 1004 of the head 1002 and lip 1043 of the forehead support 1040 is adapted to engage lip 1005 of the support post 1010. In another embodiment of the invention, the support post 1010 is co-molded to the forehead support 1040.

Figure 14:
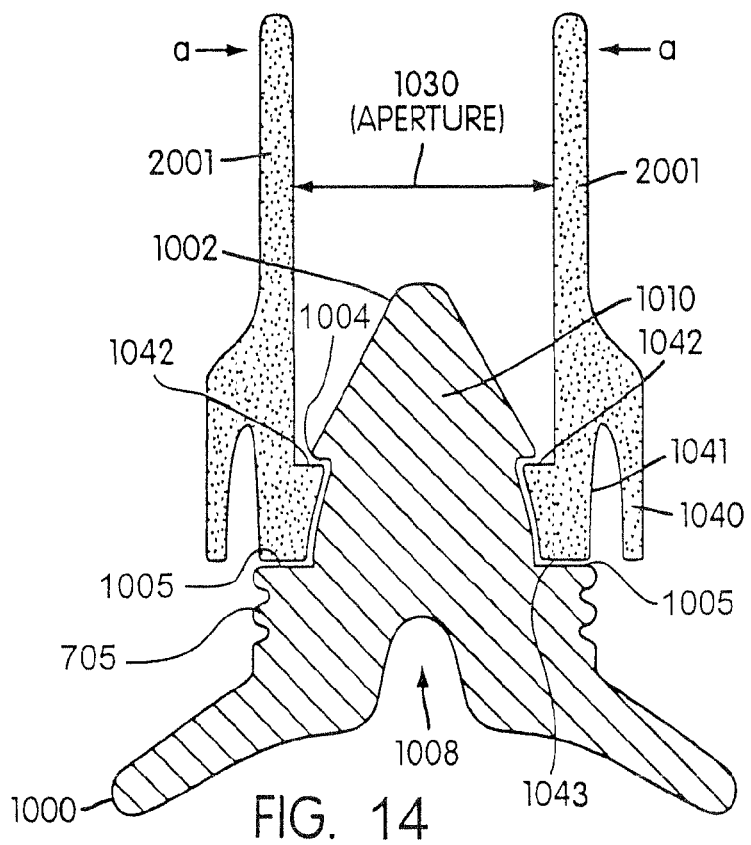
FIG. 14 is a cross-sectional view of another embodiment of a forehead pad engaged with another embodiment of a forehead support.
Figure 15:
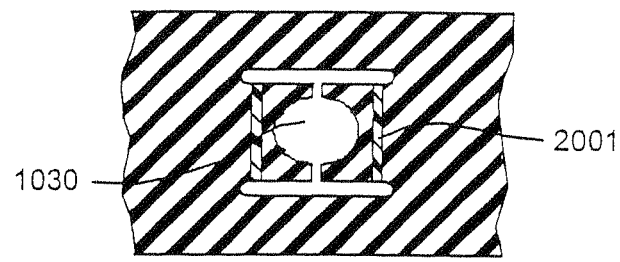
FIG. 15 is a top view of the embodiment of the forehead support shown in FIG. 14.
Figure 16:
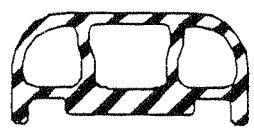
FIG. 16 is a cross-section of a prior art forehead pad.
Figure 17:
FIG. 17 is a cross-section of the forehead pad shown in FIG. 16 in a compressed state.
Figure 18:
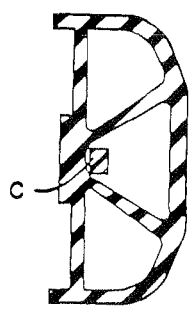
FIG. 18 is a cross-section of a prior art forehead pad.
Figure 19:
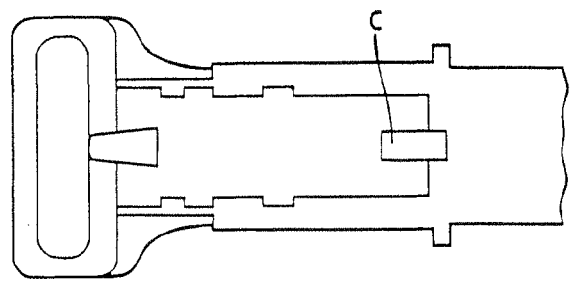
FIG. 19 is a front view of a prior art forehead support.
Figure 20:
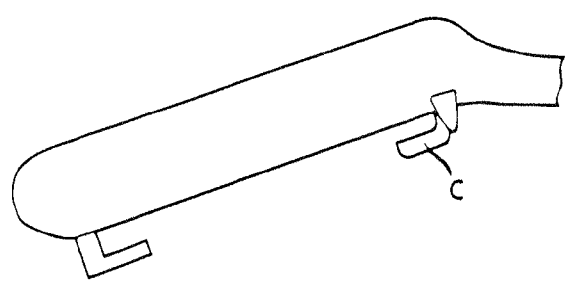
FIG. 20 is a top view of the forehead support shown in FIG. 19.
Figure 21:
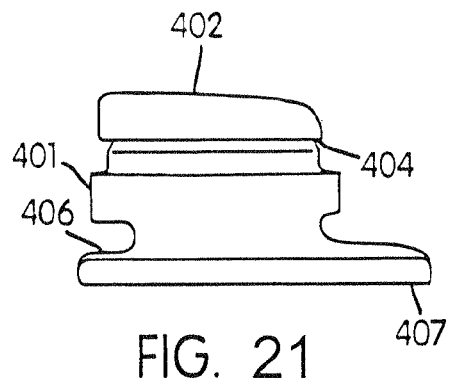
FIG. 21 is a side view of another embodiment of a forehead pad according to the present invention.
Figure 22:
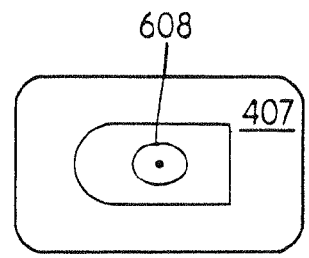
FIG. 22 is a bottom view of the embodiment shown in FIG. 21.
Figure 23:
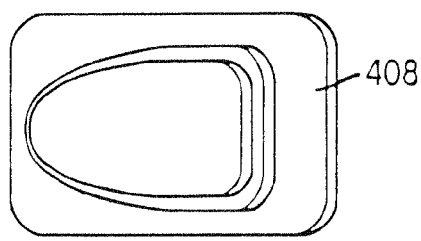
FIG. 23 is a top view of the embodiment shown in FIG. 21.
Figure 24:
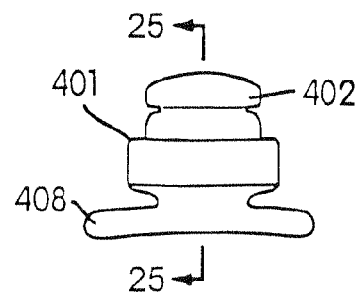
FIG. 24 is another side view of the embodiment shown in FIG. 21.
Figure 25:
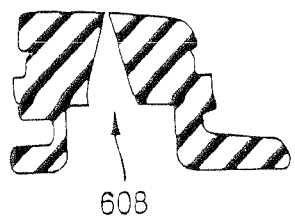
FIG. 25 is a cross-sectional view of the embodiment shown in FIG. 24 along axis 25-25.
Figure 26:
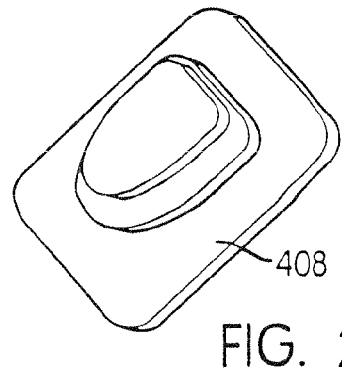
FIG. 26 is a perspective view of the embodiment shown in FIG. 21.
Figure 27:
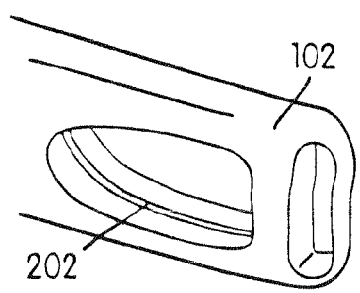
FIG. 27 is a perspective view of another embodiment of a forehead support according to the present invention.
Figure 28:
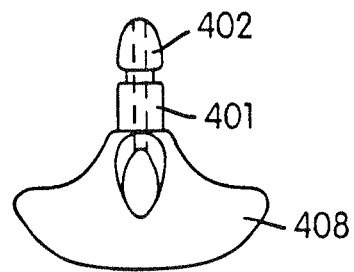
FIG. 28 is an end view of another embodiment of a forehead pad according to the present invention.
Figure 29:
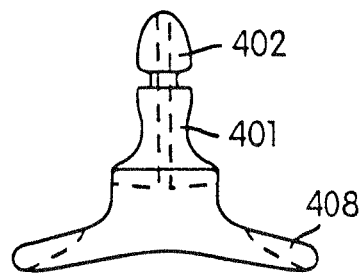
FIG. 29 is a side view of the embodiment shown in FIG. 28.
Figure 30:
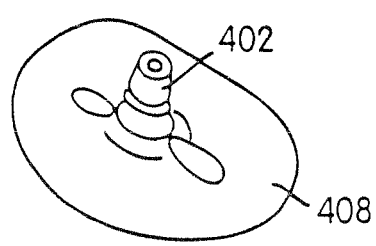
FIG. 30 is a perspective view of the embodiment shown in FIG. 28.
Figure 31:
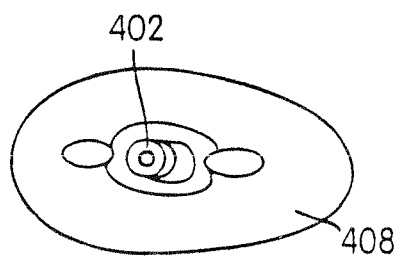
FIG. 31 is a top view of the embodiment shown in FIG. 28.
Figure 32:
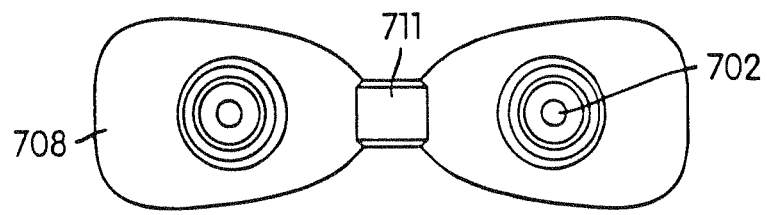
FIG. 32 is a rear view of the embodiment shown in FIG. 9.
Figure 33:
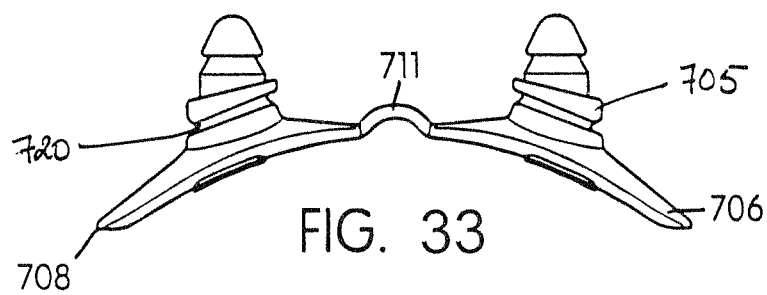
FIG. 33 is a top view of the embodiment shown in FIG. 32.
Figure 34:
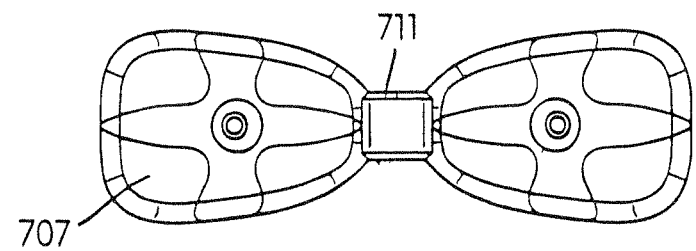
FIG. 34 is a front view of the embodiment shown in FIG. 32.
Figure 35:
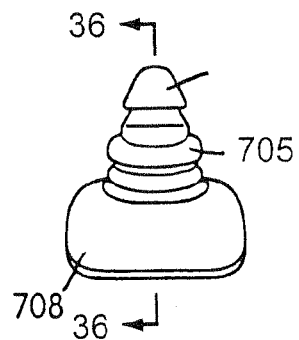
FIG. 35 is an end view of the embodiment shown in FIG. 9.
Figure 36:
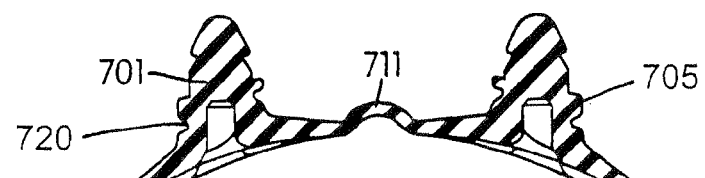
FIG. 36 is a cross-sectional view of the embodiment shown in FIG. 35 along axis 36-36.

FIGS. 14 and 15 shown another embodiment of a forehead pad 1000 engaged with an embodiment of a forehead support 1040. The forehead support 1040 has arms 2001. These arms 2001 define the aperture 1030 and can be moved in direction a to allow for removal of the pad 1000.

Figure 47:
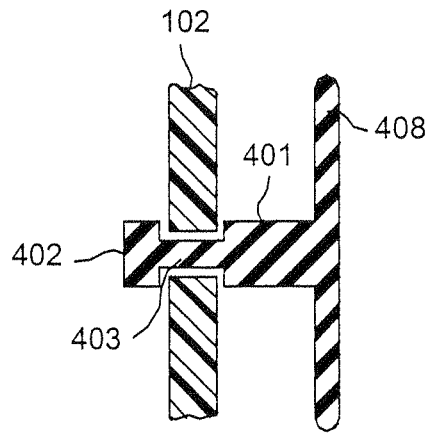
FIG. 47 is a cross-sectional view of another embodiment of a forehead pad engaged with another embodiment of a forehead support according to the present invention.
Figure 48:
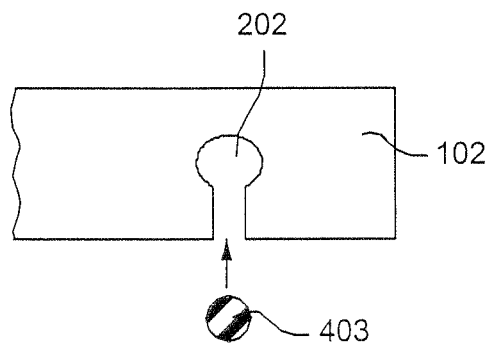
FIG. 48 is a top view of the embodiment of the forehead pad and the embodiment of the forehead support shown in FIG. 47.
Figure 49:
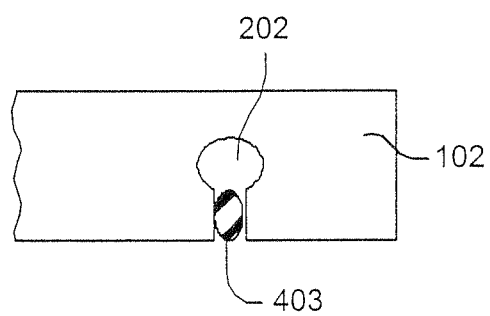
FIG. 49 is a top view of the embodiment of the forehead pad engaged with the embodiment of the forehead support shown in FIG. 47 during an intermediate assembly step.
Figure 50:
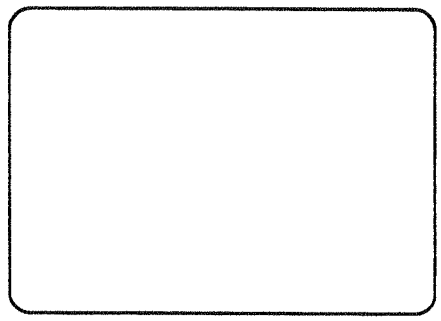
FIG. 50 is a front view of a prior art forehead pad.
Figure 51:
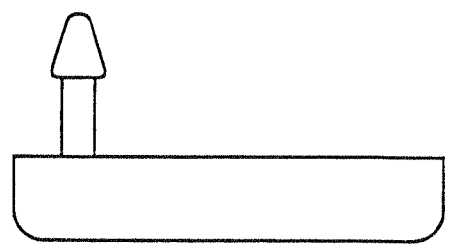
FIG. 51 is a top view of the forehead pad shown in FIG. 50.
Figure 52:
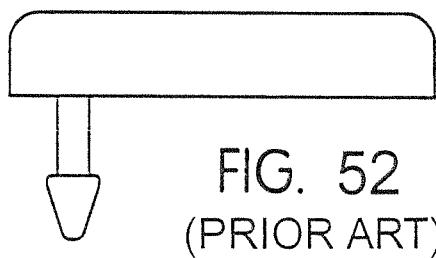
FIG. 52 is bottom side view of the forehead pad shown in FIG. 50.
Figure 53:
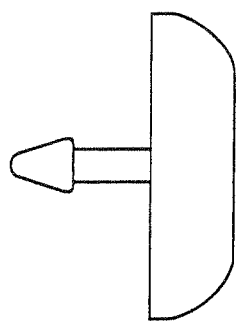
FIG. 53 is a left view of the forehead pad shown in FIG. 50.
Figure 54:
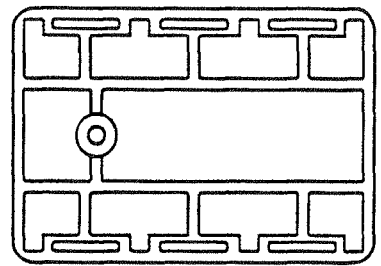
FIG. 54 is a top view of a prior art forehead pad.
Figure 55:
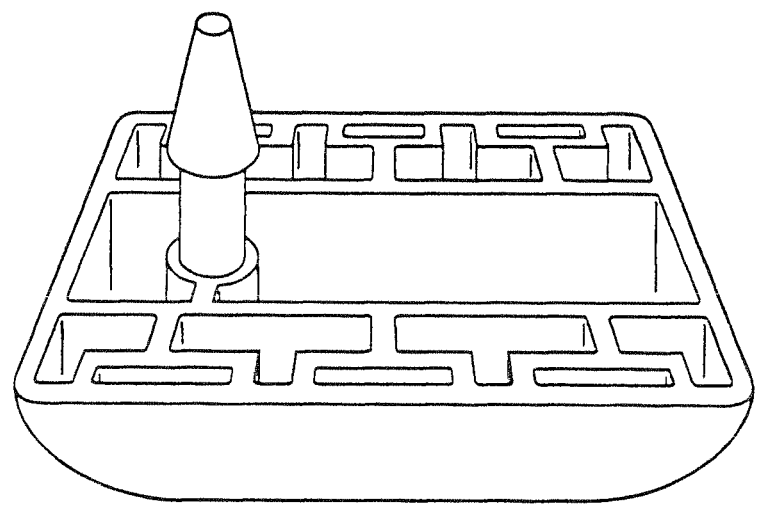
FIG. 55 is a perspective view of the forehead pad shown in FIG. 55.
Figure 56:
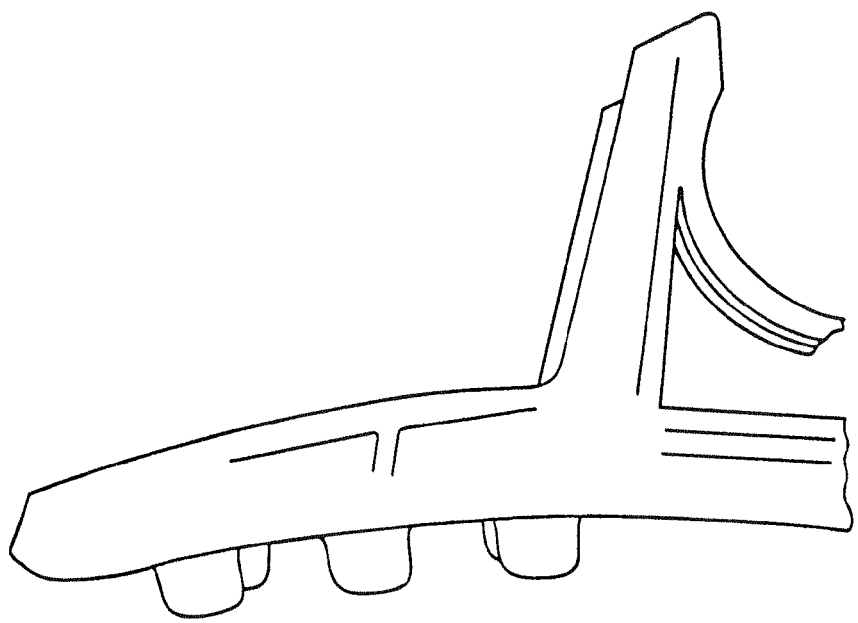
FIG. 56 is a top view of a prior art forehead support.
Figure 57:
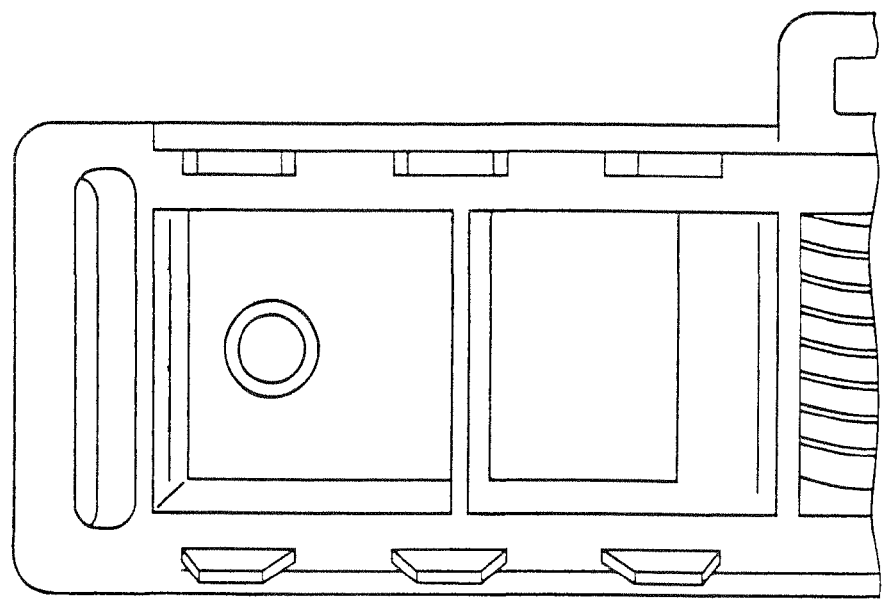
FIG. 57 is a front view of a prior art forehead support.

In another embodiment of the invention, the support post 1010 includes a generally cylindrical end region adapted to engage with a key-shaped slot of a forehead support. To attach the stalk to the forehead support, a small-diameter portion of the end region is slid through a generally rectangular region of smaller diameter, causing it to distort, before being received within a generally cylindrical region having a diameter slightly larger than that of the stalk, as in FIGS. 47 to 49. The smaller diameter portion of the end region defines two shoulder regions, similar in function to those of other embodiments, adapted to prevent axial movement of the pad.

In one form, the base portion 408 of the forehead pad is generally plate- or disc-shaped. In a preferred form, it presents a concave surface to a forehead of a patient in use. Possible shapes of the base portion include rectangular and oval shapes.

The shape of the support post 401 and base portion 408 are designed to cause lines of force 490 to be smoothly and evenly carried from the support post 401 to the base portion 408, as shown in FIG. 58. In this way there is an even distribution of pressure across the user's forehead 813. The lines of force 490 are not concentrated. The support post 401 is of a design to be sufficiently rigid so that it does not buckle when inserted and pushed.

An alternative embodiment of a forehead pad according to the present invention is shown in FIGS. 59 to 62. In this embodiment, there is a "cleat" on the T-bar arm of the forehead support, the cleat having a generally oval shape and positioned away from the surface of the arm of the forehead support, defining a space between the front side of the cleat and the arm of the forehead support. The pad has a generally oval shape, defining a major and minor axis and includes a shaft therethrough with a varying profile. The initial profile is of a complementary shape to the cleat, allowing the pad to fit on the cleat. Further along the shaft, the profile rotates approximately 90°, defining a shoulder region. In this way, the pad can be inserted over the cleat and then twisted approximately 90° to lock it in position. In this position, the shoulder region of the pad engages with the front side of the cleat.

In a preferred embodiment, the pad includes a pair of dimples adapted to engage with corresponding protrusions on the arm of the forehead support. Engagement between the dimples and respective protrusions provides feedback to the user that the pad has been correctly rotationally aligned. Furthermore, the engagement between dimples and protrusions reduces unintentional rotational movement of the pads. Alternative locking mechanisms, such as those with keys or moveable slider blocks, fall within the scope of the invention.

Figure 63:
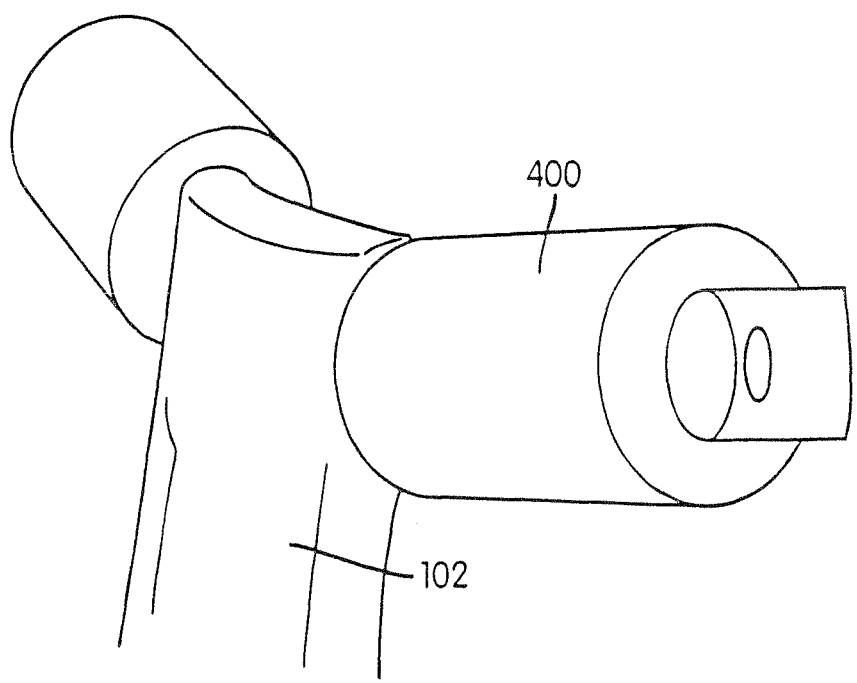
FIG. 63 is a perspective view of another embodiment of a forehead pad according to the present invention.

FIG. 63 shows an alternative embodiment of the invention. In this embodiment, the arms of the forehead support 102 are generally cylindrical and are covered in a generally cylindrical "pipe" of foam, forming the forehead pad 400. Because of the generally constant radius of the forehead arm and the pipe, there are no sharp edges presented to the forehead of the user, regardless of the angle of the support with respect to the forehead. In one form, the foam only partly surrounds the arm of the forehead support. Furthermore, because of the generally constant properties of the foam with respect to angular position, the lines of force are smoothly carried to the forehead of the user. In another embodiment, the pipe is shaped so that its outer surface positions a thicker section at the forehead and the bore through the pipe need not be circular, permitting attachment to non-circular arms.

Figure 64:
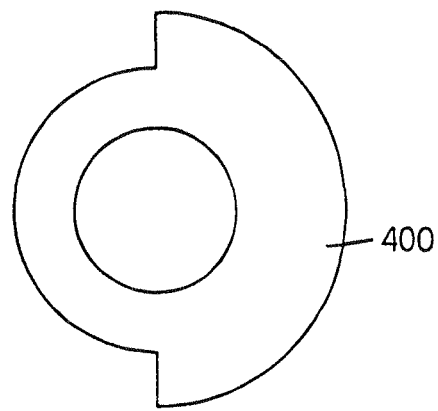
FIG. 64 is a cross-sectional view of another embodiment of a forehead pad according to the present invention.
Figure 65:
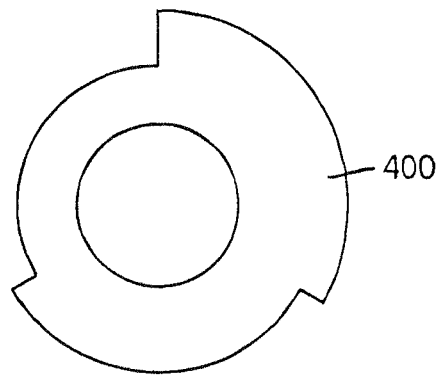
FIG. 65 is a cross-sectional view of another embodiment of a forehead pad according to the present invention.
Figure 66:
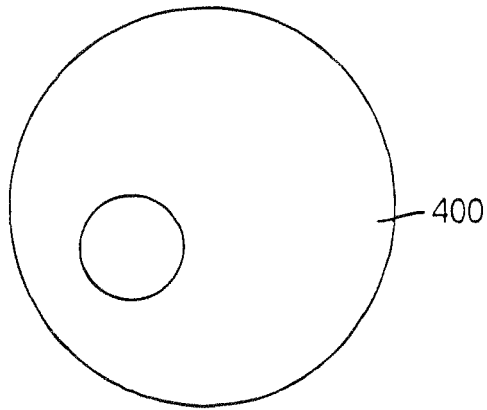
FIG. 66 is a cross-sectional view of another embodiment of a forehead pad according to the present invention.

In alternative embodiments, shown in FIGS. 64 to 66, the thickness of the pipe about a circumference can be varied to provide adjustability. The pipe can have two sections of different thicknesses (FIG. 64), three sections of different thickness (FIG. 65), or can have an eccentric thickness (FIG. 66). These embodiments offer several other advantages including increasing the snugness of the fit without removal of the mask, decreasing tightness of the pipe and associated symptoms, e.g., sweating and discomfort, without removal of the mask.

Figure 67:
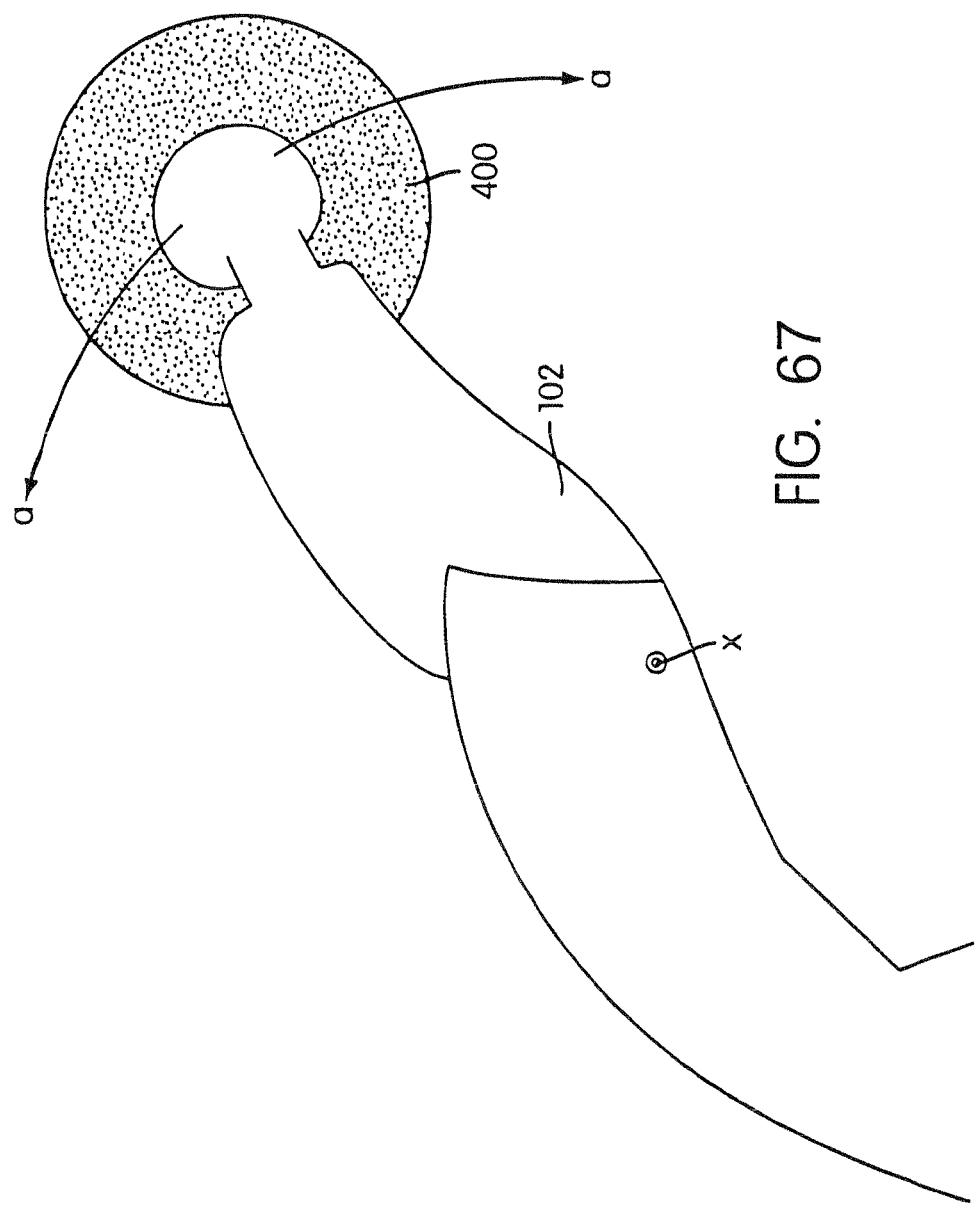
FIG. 67 is a partial cross-sectional view another embodiment of a forehead pad according to the present invention.
Figure 68:
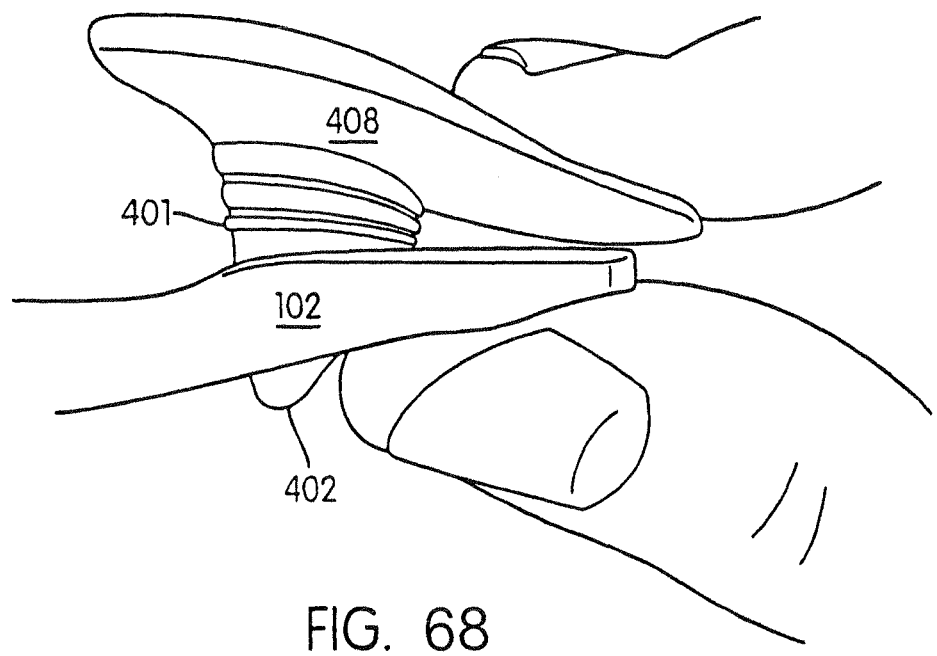
FIG. 68 shows an embodiment of a forehead pad according to the present invention flexed in a first direction.
Figure 69:
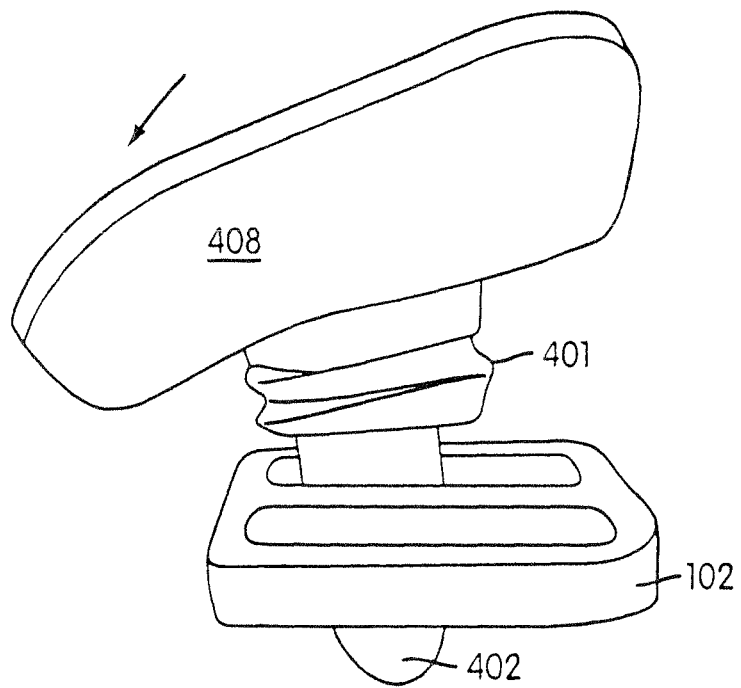
FIG. 69 shows an embodiment of a forehead pad according to the present invention flexed in a second direction.
Figure 70:
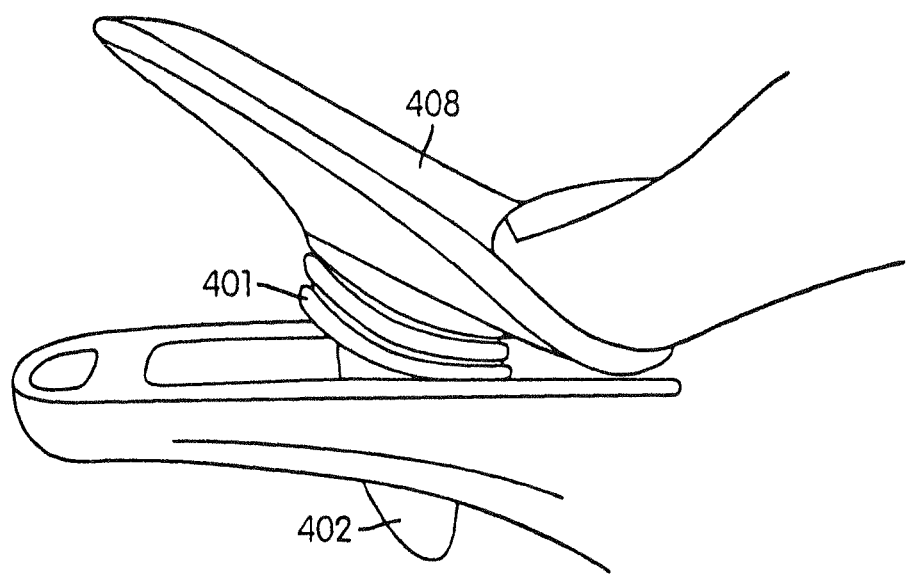
FIG. 70 shows an embodiment of a forehead pad according to the present invention flexed in a third direction.
Figure 71:
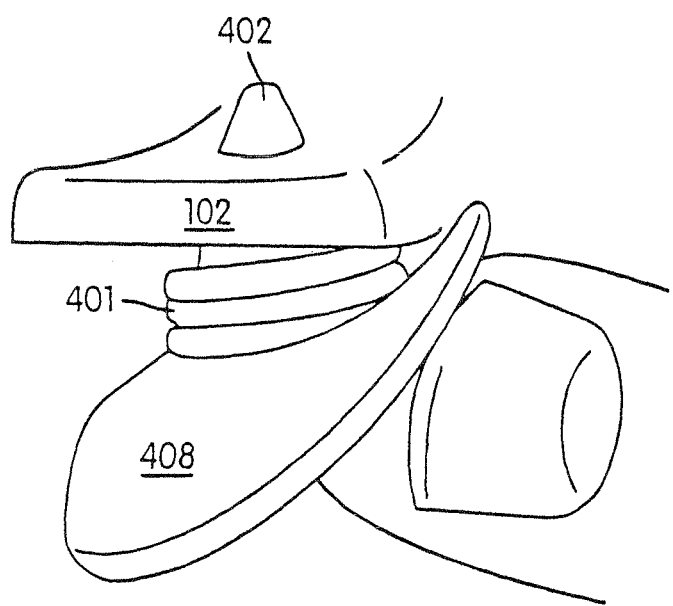
FIG. 71 shows an embodiment of a forehead pad according to the present invention flexed in a fourth direction.

FIG. 67 shows an alternative embodiment of the invention. In this embodiment, the tip of the forehead support 102 comprises a generally spherical ball. A foam or silicone pad 400, also generally spherically shaped, is placed over the tip of the forehead support 102. The general spherical shape smoothly carries lines of force from the tip of the forehead support to the forehead, regardless of orientation. In this way there is an even distribution of force on the forehead of the user.

While this application has described a few embodiments of forehead pads and forehead supports, it is well understood by one skilled in the art that various forehead pads, forehead supports, and masks can be used interchangeably. A type of forehead pad is not limited to a particular forehead support or to a specific mask.

In an alternative embodiment, the support post of the forehead pad can be used in combination with an extruded pad such as used on the MIRAGE mask (U.S. Pat. No. 6,119,693). Another embodiment has a forehead pad devoid of a convex surface, instead including a support post used in combination with a concave surface. Another embodiment includes a pad with varying cross-sectional thicknesses, e.g., it could be thinner at edges for greater flexibility when rolling, than at the center.

It can thus be appreciated that the aspects of the present invention have been fully and effectively accomplished. The foregoing specific embodiments have been provided to illustrate structural and functional principles of the present invention, and are not intended to be limiting. To the contrary, the present invention is intended to encompass all modifications, alterations and substitutions within the spirit and scope of the present invention.

What is claimed is:

1. A forehead pad comprising:
   a) a base portion, wherein the base portion defines
      (i) a first surface, and
      (ii) a second surface to contact a user's forehead, wherein the second surface is curved;
   b) a support post, wherein the support post projects from the first surface and comprises a necked down region; and
   c) a head adapted to connect the support post to a forehead support of a respiratory mask, wherein the necked down region facilitates releasable engagement of the forehead pad with the forehead support, wherein the support post further includes at least one cut away portion, the support post further comprising an undercut positioned between the at least one cut away portion and the base portion,
   wherein the cut away portion extends to a first distance from a longitudinal axis of the support post, the head extends to a second distance from the longitudinal axis of the support post and the first distance is greater than the second distance.

2. A forehead pad according to claim 1, wherein the support post projects from the base portion and is integrally molded therewith.

3. A forehead pad according to claim 2, wherein the base portion and support post include a hollowed out region extending a pre-determined distance into at least one of the base portion and support post.

4. A forehead pad according to claim 3, wherein the support post includes a tapered portion such that a region at the base portion is larger than the head.

5. A forehead pad according to claim 4, wherein the head is tapered from a bottom portion of the head to a top surface of the head.

6. A forehead pad according to claim 5, wherein a cross-sectional area of the necked down region is less than a cross-sectional area of a base of the head.

7. A forehead pad according to claim 6, wherein the support post is axially compressible.

8. A forehead pad according to claim 7, wherein the head is adapted to be releasably connected to the forehead support using a push-on motion.

9. A forehead pad according to claim 7, wherein the support post projects from the first surface of the base portion at an angle, the angle being defined between an axis of the support post and a tangent to the first surface at the point of contact between the support post and the base portion, and the angle is less than 90 degrees.

10. A forehead pad according to claim 9, wherein the head is configured so that engaging the head with the forehead support is easier than disengaging the head from the forehead support.

11. A forehead pad according to claim 9, wherein a portion of the second surface to contact a user's forehead further comprises a raised surface pattern and the raised surface pattern has four arms that extend generally from a central point of the second surface.

12. A forehead pad according to claim 11, wherein the raised surface pattern reduces the possibility of a suction effect of the forehead pad.

13. A forehead pad according to claim 11, wherein in top view a first portion of the head has a substantially rectangular shape that merges with a second portion that has a substantially triangular shape, and the forehead support has at least one aperture with a similar shape that is designed to receive the head of the forehead pad.

14. A forehead pad according to claim 13, wherein the support post is sufficiently rigid to distribute lines of force from the forehead support evenly across the second surface of the forehead pad.

15. A forehead pad according to claim 13, wherein the support post and the base portion are configured to evenly distribute forces across the second surface without localized pressure points.

16. A forehead pad according to claim 13, wherein the support post is substantially centrally mounted on the second surface.

17. A forehead pad according to claim 1, wherein the base portion has a substantially rectangular shape.

18. A forehead pad according to claim 1, wherein a shape of the head in top view comprises a first portion at least partially defined by two lines that are substantially parallel, the shape of the head in top view further comprising a second portion in which the two lines converge toward each other.

19. A forehead pad according to claim 1, wherein the at least one cut away portion is between the necked down region and the base portion.

20. A forehead support assembly for a respiratory mask, comprising:
   a forehead support comprising a pair of apertures, the pair of apertures being provided on opposites sides of a centerline of the forehead support, each aperture extending through the forehead support from a first side to a second side opposite the first side and configured to face a patient's forehead; and
   a forehead pad assembly repeatably attachable to and detachable from the forehead support, the forehead pad assembly comprising a pair of forehead pads, the forehead pad assembly being formed of flexible material, each forehead pad comprising a curved base portion having a first side configured to face the forehead support when the forehead pad assembly is connected to the forehead support and a second side configured to engage the patient's forehead;
   a support post extending from the first side of the base portion, the support post having a proximal end adjacent the first side of the base portion and a distal end opposite the proximal end, the support post comprising a head at the distal end, a first region between the head and the proximal end and a second region between the head and the proximal end, the first region being a necked down region having a cross-sectional area smaller than a cross-sectional area of a base of the head such that a lip is formed between the base of the head and the necked down region, the second region extending to a first distance from a longitudinal axis of the support post, the base of the head having a cross-sectional area that is larger than a cross-sectional area of the apertures of the forehead support and extending from the longitudinal axis of the support post to a second distance that is less than the first distance; and a hollowed out region extending a predetermined distance through the base portion;

the forehead pad assembly further comprising a connector that connects the base portions, wherein the forehead pad assembly is attachable to the forehead support by applying an axial force on each base portion in an axial direction of each support post to insert each support post through a respective aperture in the forehead support to distort the head and the lip until the lip reaches an end of the aperture and returns to its undistorted shape and engages a surface of the forehead support surrounding the aperture, and the forehead pad assembly is detachable from the forehead support by applying a pulling force to each base portion in a direction opposite to the pressure applied for insertion to distort the lip and the head to disengage the lip from the surface of the forehead support.

21. A forehead support assembly for a respiratory mask, claim 20, wherein the support post of each forehead pad projects from the first side of the base portion at an angle, the angle being defined between an axis of the support post and a tangent to the first side at the point of contact between the support post and the base portion, and the angle is less than 90 degrees.

22. A forehead support assembly for a respiratory mask according to claim 21, wherein a portion of the second side of each forehead pad further comprises a raised surface pattern and the raised surface pattern has four arms that extend generally from a central point of the second side.

23. A forehead support assembly for a respiratory mask according to claim 22, wherein a first portion of the each of the heads has a substantially rectangular shape that merges with a second portion that has a substantially triangular shape, and each aperture of the forehead support has a similar shape.

24. A forehead support assembly for a respiratory mask according to claim 23, wherein the raised surface pattern reduces the possibility of a suction effect of each of the forehead pads.

25. A forehead support assembly for a respiratory mask according to claim 20, wherein the second region of the support post is a cut away portion between the necked down region and the proximal end.

26. A forehead support assembly for a respiratory mask according to claim 20, wherein the hollowed out region extends into the support post without reaching the head.

27. A one-piece integrally molded forehead pad comprising:
a substantially rectangular base portion having a first side and an opposing second side, the first side being concavely curved and having a raised surface pattern, the second side being convexly curved;
a support post projecting from the second side of the base portion at an oblique angle defined between a tangent to the second side of the base portion at a point of contact between the support post and the base portion, the support post comprising at least one undercut adapted to increase a flexibility of the support post;
a hollowed out region extending through the base portion and partly into the support post, the hollowed out region configured to make the support post axially compressible;
a head adapted to connect the forehead pad to a forehead support of a respiratory mask, a top surface of the head having a substantially rectangular first portion that merges with a substantially triangular second portion, the head being tapered from a bottom portion to the top surface and extending to a first distance from a longitudinal axis of the support post; and
a necked down region located between the support post and the head, a cross-sectional area of the necked down region being smaller than a cross-sectional area of a top portion of the support post and smaller than a cross-sectional area of the bottom portion of the head so as to form a first lip at a base of the head and a second lip at the top portion of the support post,
wherein the support post includes a tapered portion such that a region at the base portion has a larger cross-sectional area than the head, and
wherein a portion of the support post extends to a second distance from the longitudinal axis of the support post, the first distance being less than the second distance.

28. The forehead pad of claim 27, wherein support post is flexible and is adapted to withstand an assembly force applied when the forehead pad is connected to the forehead support of the respiratory mask.

29. The forehead pad of claim 27, wherein the hollowed out region imparts a degree of springiness to and flexibility to the forehead pad.

30. A one-piece integrally molded forehead pad assembly comprising:
two forehead pads according to the forehead pad of claim 27; and
at least one connector that connects adjacent base portions.

31. The forehead pad assembly of claim 30, wherein the connector is a flexible bridge.

32. A respiratory mask assembly comprising:
a headgear assembly adapted to support the mask assembly on a user's face;
a frame portion with lower headgear anchor points adapted to anchor straps of the headgear assembly;
a seal-forming portion adapted to cover the user's nose and/or mouth;
a forehead support connected to the frame portion, the forehead support being curved and having a plurality of headgear connection points and one or more forehead pad connection points; and
the forehead pad assembly of claim 30, wherein
the forehead pad connection points comprise apertures shaped complimentary to the shapes of the heads of the forehead pads, the forehead pad connection points receiving the heads of the forehead pads,
the heads of the forehead pads have larger cross-sectional areas than the forehead pad connection point apertures,
a length of each necked down region is substantially the same as a length of the forehead pad connection point apertures,
the first lip of each forehead pad abuts a first side of the forehead support and the second lip of each forehead pad abuts a second side of the forehead support when the forehead pad assembly is mounted on the forehead support,
the emergence of the heads of the forehead pads through the forehead connection points produces an audible sound, and
the headgear connection points comprise apertures that receive headgear straps to secure the mask assembly to the user's face.

33. The respiratory mask assembly of claim 32, wherein the curvature of the forehead support is adapted to follow a curvature of the user's forehead.

34. The respiratory mask assembly of claim 33, wherein the first lips and the second lips of the forehead pads prevent axial movement within the forehead pad connection points when the forehead pad assembly is mounted on the forehead support.

35. The respiratory mask of claim 34, wherein the head and the first lip are configured to distort when an axial force is applied to a first end of the hole in the forehead support until the head and the first lip reach a second end of the hole in the forehead support.

36. The forehead pad of claim 27, wherein the first and/or second surface of the base portion has a sand-blasted finish.

37. The forehead pad of claim 27, wherein, in the absence of a force acting on the support post, the support post projects from the second side of the base portion at the oblique angle defined between the tangent to the second side of the base portion at the point of contact between the support post and the base portion.

38. The forehead pad of claim 27, wherein the hollowed out region does not extend into the head.

39. The forehead pad of claim 27, wherein the support post further comprises a cut away portion between an undercut and the necked down region.

40. A silicone forehead pad comprising:
    a substantially rectangular base portion;
    a support post projecting from the base portion and comprising at least one cut-away portion adapted to increase a flexibility of the support post, the cut-away portion extending to a first distance from a longitudinal axis of the support post;
    a hollowed out region extending through the base portion and partly into the support post, the hollowed out region being configured to make the support post axially compressible;
    a head adapted to connect the forehead pad to a forehead support of a respiratory mask, a top surface of the head having a smaller cross-sectional area than a base of the head, the head extending from the longitudinal axis of the support post to a second distance that is less than the first distance; and
    a necked down region located between the support post and the head,
    wherein the support post includes a tapered portion such that a region at the base portion has a larger cross-sectional area than the head.

41. The forehead pad of claim 40, wherein the support post projects from the base portion at an angle defined between a tangent to the second surface of the base portion at a point of contact between the support post and the base portion.

42. The forehead pad of claim 41, wherein the angle is an oblique angle.

43. The forehead pad of claim 40, wherein the necked down region forms a first lip at the base of the head and forms a second lip at a top portion of the support post.

44. The forehead pad of claim 40, wherein the hollowed out imparts a degree of springiness to and flexibility to the forehead pad.

45. The forehead pad of claim 44, wherein the support post is adapted to withstand forces needed for assembly of the head to the forehead support.

46. The forehead pad of claim 40, wherein the head has a substantially rectangular first portion that merges with a substantially triangular second portion.

47. The forehead pad of claim 40, wherein the base portion is curved and has a raised surface pattern.

48. A one-piece integrally molded forehead pad assembly comprising:
    two forehead pads according to the forehead pad of claim 40; and
    at least one connector that connects adjacent base portions.

49. A respiratory mask assembly comprising:
    a frame portion;
    a seal-forming portion adapted to cover the user's nose and/or mouth;
    a forehead support connected to the frame portion, the forehead support being curved and having a plurality forehead pad connection points; and
    the forehead pad assembly of claim 48 connected to the forehead support.

50. The respiratory mask assembly of claim 49, wherein the necked down region forms a first lip at the base of the head and forms a second lip at a top portion of the support post.

51. The respiratory mask of claim 50, wherein the head and the first lip are configured to distort when an axial force is applied to a first end of the hole in the forehead support until the head and the first lip reach a second end of the hole in the forehead support.

52. The forehead pad of claim 40, wherein the hollowed out region terminates before reaching the head.

* * * * *